(12) United States Patent
Chiang et al.

(10) Patent No.: US 6,949,660 B2
(45) Date of Patent: Sep. 27, 2005

(54) CHIRAL (1PYRROLINO) FULLERENE DERIVATIVES

(75) Inventors: Long Y. Chiang, Acton, MA (US); Vijayaraj Anantharaj, Piscataway, NJ (US); Manas Kumar Haldar, Taipei (TW)

(73) Assignee: Seth Nanotechnology, Incorporated, Sugar Land, TX (US)

( * ) Notice: Subject to any disclaimer, the term of this patent is extended or adjusted under 35 U.S.C. 154(b) by 146 days.

(21) Appl. No.: 10/437,410

(22) Filed: May 13, 2003

(65) Prior Publication Data

US 2004/0034205 A1 Feb. 19, 2004

Related U.S. Application Data

(63) Continuation-in-part of application No. 10/201,798, filed on Jul. 24, 2002, now Pat. No. 6,576,655, which is a division of application No. 09/521,025, filed on Mar. 6, 2000, now Pat. No. 6,455,709, which is a continuation-in-part of application No. 08/976,532, filed on Nov. 20, 1997, now Pat. No. 6,046,361, which is a continuation-in-part of application No. 08/893,055, filed on Jul. 15, 1997, now abandoned, which is a continuation-in-part of application No. 08/547,714, filed on Oct. 26, 1995, now Pat. No. 5,648,523.

(51) Int. Cl.$^7$ .......................................... C07D 405/00
(52) U.S. Cl. ..................................................... 548/517
(58) Field of Search ........................................ 548/517

(56) References Cited

U.S. PATENT DOCUMENTS

| | | | |
|---|---|---|---|
| 5,177,248 A | 1/1993 | Chiang et al. ................. | 560/86 |
| 5,294,732 A | 3/1994 | Chiang et al. ................. | 560/86 |
| 5,416,188 A | 5/1995 | Chiang et al. ............... | 528/291 |
| 5,648,523 A * | 7/1997 | Chiang ........................ | 562/100 |
| 5,717,076 A * | 2/1998 | Yamamoto et al. ......... | 534/558 |
| 5,811,460 A | 9/1998 | Friedman et al. ........... | 514/563 |
| 6,046,361 A * | 4/2000 | Chiang ........................ | 564/458 |
| 6,303,760 B1 * | 10/2001 | Dorn et al. .................... | 534/11 |
| 6,380,434 B1 * | 4/2002 | Chiang ........................ | 564/458 |
| 6,399,785 B1 * | 6/2002 | Murphy et al. .............. | 548/417 |
| 6,448,412 B1 * | 9/2002 | Murphy et al. .............. | 548/417 |
| 6,455,709 B1 * | 9/2002 | Chiang et al. ............... | 549/417 |
| 6,576,655 B2 * | 6/2003 | Chiang et al. ............... | 514/417 |
| 6,593,137 B1 * | 7/2003 | Erlanger et al. ............. | 435/345 |
| 6,790,963 B2 * | 9/2004 | Chiang et al. ............... | 548/417 |

FOREIGN PATENT DOCUMENTS

| | | | | |
|---|---|---|---|---|
| DE | 42 40 042 A1 | 6/1994 | ......... | C07D/261/00 |
| EP | 0 653 424 A1 | 5/1995 | | |
| EP | 0 770 577 A1 | 5/1997 | ........... | C01B/31/02 |
| JP | 5-221623 | 8/1993 | | |
| JP | 5-294864 | 11/1993 | | |
| JP | 06336458 | 12/1994 | ......... | C07C/69/753 |
| JP | 7-89972 | 4/1995 | | |
| JP | 7-233093 | 9/1995 | | |
| JP | 8-225313 | 9/1996 | | |
| JP | 8-245209 | 9/1996 | | |
| JP | 2000290278 | 10/2000 | ....... | C07D/401/043 |
| WO | WO 95/19949 | 7/1995 | | |

OTHER PUBLICATIONS

Gan et al., "Synthesis of fullerene Amino Acid Derivatives by Direct Interaction of Amino Acid Ester with $C_{60}$", *J. Org. Chem.*, 61:1954–1961, XP–001007263.

Huang et al., "Langmuir–Blodgett Film Formation of a Fullerene Dicarboxylic Acid Derivative $C_{60}$(HOOCCHNHCHCOOH) and its Photocurrent Generation", *Journal of Colloid and Interface Science*, 204:277–283, XP–001007266.

Mashino et al., "Inhibition of *E. coli* and Cancer Cell Growth By Fullerene Derivatives and the Inhibition Mechanism", *Electrochemical Society Proceedings*, 2000–11:244–249, 2000, XP–001007720.

Shi et al., "Photoelectric Conversion Property of Monolayer Films of Fullerene Tetracarboxylic Acid Derivatives", *Thin Solid Films*, 352:218–222, 1999, XP–001007611.

Tabata et al., "Biological Functions of Fullerene", *Pure Appl. Chem.*, 71:2047–2053, 1999, XP–001007556.

Wu et al., "Photoinduced Reaction of [60]Fullerene With Tertiary Amines:Synthesis of [60]Fulleropyrrolidines", *Synthetic Communications*, 27:2289–2298, 1997, XP–001007852.

Wu et al., "Syntheisi Derivatives of 2',5'–Dihydropyrrolo '3',4':1,2!'60!Fullerene", *Acta Chimica Sinica*, 57:812–819, 1999, XP–001007214.

Belik et al., "Reaction of Buckminsterfullerene with orth–Quinodimethane; a New Access to Stable $C_{60}$ Derivatives," Angew. Chem. Int. Ed. Engl. 1:78–80, 1993.

Chiang et al., "Efficient Synthesis of Polyhydroxylated Fullerene Derivatives via Hydrolysis of Polycyclosulfated Precursors," J. Org. Chem., 59:3960–3968, 1994.

Chiang et al., "Evidence of Hemiketals Incorporated in the Structure of Fullerols Derived from Aqueous Acid Chemistry," J. Am. Chem. Soc., 115:5453–5457, 1993.

(Continued)

*Primary Examiner*—Deborah C. Lambkin

(57) ABSTRACT

An E-isomeric fulleropyrrolidine compound of formula (I):

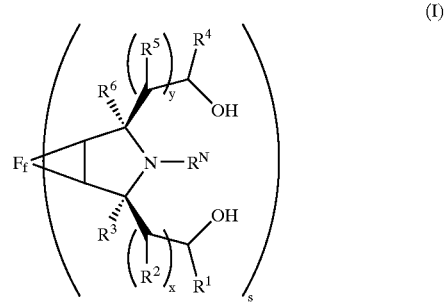

is disclosed. Also disclosed is a method for preparing and polymers prepared from such a compound.

60 Claims, No Drawings

OTHER PUBLICATIONS

Chiang et al., "Free Radical Scavenging Activity of Water–Soluble Fullernois," J. Chem. Soc. Chem. Commun., 1283–1284, 1995.

Chiang et al., "Multi–hydroxy Additions onto $C_{60}$ Fullerene Molecules," J. Chem. Soc. Chem. Commun., 1791–1793, 1992.

Chiang et al., "Versatile Nitronium Chemistry for $C_{60}$ Fullerene Fnctionalization," J. Am. Chem. Soc., 114:10154–10157, 1992.

Friedman et al., "Inhibition of the HIV–1 Protease by Fullerene Derivatives: Model Building Studies and Experimental Verification," J. Am. Chem. Soc., 115:6506–6509, 1993.

Hirsch et al., "Global–Trotting Hydrogens on The Surface of The Fullerene Compound $C_{60}H_6(N(CH_2CH_2)_2O)_6$," Angew. Chem. Int. Ed. Engl. 30:1309–1310, 1991.

Hoke et al., "Reaction of Fullerences and Benzyne," J. Org. Chem. 57:5069–5071, 1992.

Isaacs et al., "Improved Purification of $C_{60}$ and Formation of γ and π–Homoaromatic Methano–Bridged Fullerene by Reaction with Alkyl Diazoacetates," Helvetica Chimica Acta 76:1231–1250, 1993.

Juha et al., "Reactivity of Rullerenes with Chemically Generated Singlet Oxygen," J. Chem. Soc., *Chem. Commun.*, 2437–2438, 1994.

Krusic et al., "Radical Reactions of $C_{60}$," Science 254:1183–1185, 1991.

Li et al., "$C_{60}$ Fuijerol Formation Catalysed by Quaternary Ammonium Hydroxides," J. Chem. Soc., Chem. Commun. 1784–1785, 1993.

Paulus et al., "Diethyl Methano–$C_{60}$–Fullerene–61, 61–Dicarboxylate Chloroform Solvate at 193K, $C_{60}C(CO_2C_2H_5)_2CHCl_3$," Acta Cryst, C51:143–146, 1995.

Prato et al., "[3+2] and [4+2] Cycloadditions of $C_{60}$," J. Am. Chem. Soc. 115:1594–1595, 1993.

Shu et al., "Reaction of [80] Fullerene with 1–4–Methoxyphenyl)–1–(Trimethylsilyloxy) Ethylene," J. Chem. Commun. 367–368, 1995.

Roy et al., "$NO_2$ Adducts of $C_{60}$: Synthesis of Polynitro–Polyhydroxy Fullerenes," J. Chem. Soc., Chem. Commun., 275–276, 1994.

Schneider et al., "Formation of Fullerols Via Hydrobotation of Fullerene–$C_{60}$," J. Chem. Soc., Chem. Commun., 463–464, 1994.

Suzuki et al., "Systernatic Inflation of Buckminsterfullerene $C_{60}$: Synthesis of Diphenyl Fulleriods $C_{61}$ to $C_{66}$," Science 254:1186–1188, 1991.

Taliani et al., "Light–Induced Oxygen Incision of $C_{60}$," J. Chem. Soc. Chem. Commun., 220–222, 1993.

Tokuyama et al., "Photoinduced Biochemical Activity of Fullerene Carboxylic Acid," J. Am. Chem. Soc. 115:7918–7919, 1993.

Tsuda et al., "Addition Reaction of Benzyne to $C_{60}$," Chemistry Letters 2333–2334, 1992.

Wilson et al., "A New Reaction of Fullerences: [2+2] Photocycloaddition of Enones," J. Am. Chem. Soc. 115:8495–8496, 1993.

Batch et al., "Supramolecular Aggregation of an ($\pi^2$–$C_{60}$) Iridium Complex Involving Phenyl Chelation of the Fullerene," J. Am. Chem Soc. 114:5455–5457, 1992.

Chiang et al., "Pharmacology," Chemical Abstracts vol. 122, No. 23, Jun. 5, 1995, Abstract No. 281924.

Chiang et al., "Pharmacology," Chemical Abstracts vol. 124, No. 9, Feb. 26, 1996, Abstract No. 106531.

Chiang et al., "Free–Radical Scavenging Effect of Water–Soluble [60] Fullerenols in Whole Blood . . . ," Proc. Electrochem. Soc. 95–10, 699 (1995).

Huang et al., "Antiproliferative Effect of Polyhydroxylated $C_{60}$ on Vascular Smooth Muscle Cells," Proc.Electrochem. Soc. 96–10, 403 (1996).

Prato et al., "Fulleropyrrolidines: A Family of Full–Fledged Fullerene Derivatives," Accounts of Chem. Research vol. 31, No. 9, Sep. 1998, pp 519–526.

Maggini et al., "Addiion Reactions of $C_{60}$ Leading to Fulleroprolines," J. Am. Chem. Soc., Chem. Commun., 1994, pp 305–306.

Maggini et al., "Addition of Azomethine Ylides to $C_{60}$: Synthesis, Characterization, and Functionalization of Fullerene Pyrrolidines," J. Am. Chem. Soc. 1993, 115, 9798–9799.

Maggini et al., "Ferrocenyl Fulleropyrrolidines: a Cyclic Voltammetry Study," J. Chem. Soc., Chem. Commun., 1994, pp 589–590.

Bianco et al., "Synthesis, Chiroptical Properties, and Configurational Assignment of Fulleroproline Derivatives and Peptieds," J. Am. Chem. Soc.,1996, 118, 4072–4080.

Wilson et al., "Amino Acids as Precursors for N–Unsubstituted Fulleropyrrolidine Derivatives," Tetrahedron Letters, vol. 37, No. 6, pp 75–778, 1996.

Gan et al., "Synthesis of Pyrrolidine Ring–Fused Fullerene Multicarboxylates by Photoreaction," J. Org. Chem. 1998, 63, 4240–4247.

Gan et al., "Synthesis of Fullerene Amino Acid Derivatives by Direct Interaction of Amino Acid Ester with $C_{60}$," J. Org. Chem. 1996, 61, 1954–1961.

Novello et al., "Stereoselective Additions to [60] Fullerene," J. Chem. Soc., Chem. Commun., 1996, pp 903–904.

Schick et al., "Unusual Luminescence of Hexapyrrolidine Derivatives of $C_{60}$ with $T_h$ and Novel $D_3$–Symmetry," Am. Chem. Soc., 1999, pp 3246–3247.

Ishida et al., "The First 1,3–Dipolar Cycloaddition Reaction of [60] Fullerene with Thiocarbonyl Ylide," Tetrahedron Letters, 1999, vol. 40, pp 1543–1546.

Ohno et al., "Fusion of $C_{60}$ with Cyclic Amino Acid and Thioures by Hetero Diels–Alder Reactions," Heterocycles, vol. 46, 1997. pp 49–52.

Bianco et al., "Molecular Recognition by a Silica–Bound Fullerene Derivative," Am. Chem. Soc., 1997, pp 7550–7554.

Luo et al., Substituent and Solvent Effects on Photoexcited States of Functionalized Fullerence [60], J. Chem. Soc., Faraday Trans., 1998, 94(4), pp 527–532.

Zheng et al., "Preparation of Stable Nitroxides Integrated Into [70] Fullerene," Marcel Dekker, Inc., 1998, pp 879–886.

Zhou et al., "Synthesis, Langmuir–Blodgett Deposition and Optical Characterization of a 4–Acetalphenyl–Substituted $C_{60}$–Pyrrolidine Derivative $C_{60}(C_{12}H_{17}NO_2)$," J. Chem. Soc., Faraday Trans., 1997, 93(11), pp 2077–2081.

Wu et al., "Reaction of [60] Fullerene with 4–Nitro–N–Benzylbenzimidoyl Chloride and Triethylamine: A New Method for the Synthesis of [60] Fullerene–Fused Pyrroline," Marcel Dekker, Inc., 1997, pp 1415–1422.

Da Ros et al., "Easy Access to Water–Soluble Fullerene Derivatives Via 1,3–Dipolar Cycloadditions of Azomethine Ylides to $C_{60}$," J. Org. Chem., 1996, vol. 61, pp 9070–9072.

Corvaja et al., "$C_{60}$ Derivative Covalentyly Linked to a Nitroxide Radical: Time–Resolved EPR Evidence of Electron Spin Polarization by Intramolecular Radical–Triplet Pair Interaction," J. Am. Chem. Soc., 1995, vol. 117, pp 8857–8858.

Arena et al., "Synthesis and EPR Studies of Radicals and Biradical Anions of $C_{60}$ Nitroxide Derivatives," J. Am. Chem. Soc., 1997, vol. 119, pp 789–795.

Zhou et al., "Fullerene Induced C–N Bond Breaking and Formation: Synthesis of Fullerene Pyrrolidine and Methanofullerene Sarcosine Derivatives by Photochemical Addition of Sarcosine Ester to $C_{60}$," Tetrahedron Letters, 1995, vol. 36, No. 50, pp 9169–9172.

Zhou et al., "Fullerene Induced C–N Bond Breaking and Formation: Synthesis of Fullerene Pyrrolidine and Methanofullerene Sarcosine Detrivatives by Photochemical Addition of Sarcosine Ester to $C_{60}$," Tetrahedon Letters, 1995, vol. 36, No. 50, pp 9169–9172.

Iyoda et al., "Reactions of $C_{60}$ with α–Silylamine Detrivatives: Two Types of [3+2] Addition of Azomething Ylides to $C_{60}$," Chemistry Letters, 1995, pp 1133–1134.

Shu et al., "1,3–Dipolar Cycloaddition Reactionof [60] Fullerene and Imines of α–Amino Acid Esters: Formation of Fullerene–Fused Proline Derivatives," Tetrahedron Letters, 1995, vol. 36, No. 22, pp 3871–3874.

* cited by examiner

CHIRAL (1PYRROLINO) FULLERENE DERIVATIVES

CROSS REFERENCE TO RELATED APPLICATIONS

This application is a continuation-in-part of U.S. Ser. No. 10/201,798, filed Jul. 24, 2002, now U.S. Pat. No. 6,576,655, which, in turn, is a divisional application of U.S. Ser. No. 09/521,025, filed Mar. 6, 2000 now U.S. Pat. No. 6,455,709, which, in turn, is a continuation-in-part of U.S. Ser. No. 08/976,532, filed Nov. 20, 1997, now U.S. Pat. No. 6,046,361, which, in turn, is a continuation-in-part of U.S. Ser. No. 8/893,055, filed Jul. 15, 1997, now abandoned, which, in turn, is a continuation-in-part of U.S. Ser. No. 08/547,714, filed Oct. 26, 1995, now U.S. Pat. No. 5,648,523.

BACKGROUND OF THE INVENTION

Cancer remains a formidable disease with a high mortality rate in today's society. Indeed, cancer is second only to cardiovascular disease as a cause of death, killing one out of four people in developed countries.

Cancerous tumors commonly originate from normal cells which transform into malignant cells or tumors. The initial tumor growth may be slow and thus may be difficult to detect. The growth often becomes more aggressive and invasive with time, eventually spreading throughout the whole body and resulting in death.

Photodynamic therapy (PDT) is one of the methods for treating tumors. For review, see Dougherty, T. J. *Photochem. Photobiol.* 1993, 58, 895. At present, the most commonly used sensitizers for clinical PDT practices are Photofrin II, an enriched active fraction of hematoporphyrin derivatives, and disulfonated aluminum phthalocyanine. These compounds, once photoactivated, induce severe oxidative damage to the structure of lipids, proteins, and nucleic acids. Since many biologically active molecules, e.g., DNA, demonstrate higher affinity toward stereospecific ligands, it is therefore desirable to develop stereospecific PDT sensitizers to enhance cytotoxicity of such antitumor agents.

SUMMARY

An aspect of this invention relates to a compound of formula (I):

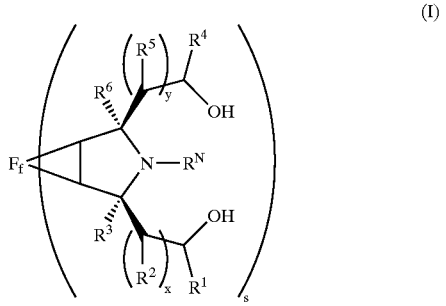

(I)

$F_f$ is $F(-K)_m(-Y-Z)_q$. F is a fullerene core. Each K, independently, is —OH, —SH, —$NH_2$, —NHOH, —$SO_3$H, —$OSO_3$H, —$CO_2$H, —$CONH_2$, —$CONHNH_2$, —P(OH)$_3$, —PO(OH)$_2$, —O—PO(OH)$_2$, —O—PO(OH)—O—PO(OH)$_2$, —O—PO($O^{31}$)—O—$CH_2CH_2$—$NH_3^+$, —O—PO($O^-$)—O—$CH_2CH_2$—$N^+(CH_3)_3$, -glycoside, —$OCH_3$, —$OCH_2(CHOH)_4$—$CH_2OH$, —$OCH_2(CHOH)_2$—$CH_2OH$, —NH—$CH_2$—$CO_2$H, —[CH($CO_2$H)—$CH_2$]$_{1-100}$—OH, —[CH($CO_2R^a$)—$CH_2$]$_{1-100}$—OH, —[C($CH_3$)($CO_2$H)—$CH_2$]$_{1-100}$—OH, —[C($CH_3$)($CO_2$ $R^a$)—$CH_2$]$_{1-100}$—OH, —N(OH)$_2$, —$NH_3^+$, —$N^+H_3R^a$, —$N^+HR^aR^b$, or —$N^+R^aR^bR^c$. Each Y is —A—B—, in which A is —O—, —NH—, —S—, —CO—O—, —O—CO—, —O—CO—O—, —O—CO—NH—, —NH—CO—NH—, —CO—NH—, or —NH—CO—; and B is —$R^a$—O—[Si($CH_3$)$_2$—O—]$_{1-100}$, $C_{1-2000}$ alkyl, $C_{6-40}$ aryl, $C_{7-2000}$ alkylaryl, $C_{7-2000}$ arylalkyl, ($C_{1-30}$ alkyl ether)$_{1-100}$, ($C_{6-40}$ aryl ether)$_{1-100}$, ($C_{7-2000}$ alkylaryl ether)$_{1-100}$, ($C_{7-2000}$ arylalkyl ether)$_{1-100}$, ($C_{1-30}$ alkyl thioether)$_{1-100}$, ($C_{6-40}$ aryl thioether)$_{1-100}$, ($C_{7-2000}$ alkylaryl thioether)$_{1-100}$, ($C_{7-2000}$ arylalkyl thioether)$_{1-100}$, ($C_{2-50}$ alkyl ester)$_{1-100}$, ($C_{7-2000}$ aryl ester)$_{1-100}$, ($C_{8-2000}$ alkylaryl ester)$_{1-100}$, ($C_{8-2000}$ arylalkyl ester)$_{1-100}$, —$R^a$—CO—O—($C_{1-30}$ alkyl ether)$_{1-100}$, —$R^a$—CO—O—($C_{6-40}$ aryl ether)$_{1-100}$, —CO—O—($C_{7-2000}$ alkylaryl ether)$_{1-100}$, —$R^a$CO—O—($C_{7-2000}$ arylalkyl ether)$_{1-100}$, ($C_{4-50}$ alkyl urethane)$_{1-100}$, ($C_{14-60}$ aryl urethane)$_{1-100}$, ($C_{10-2000}$ alkylaryl urethane)$_{1-100}$, ($C_{10-2000}$ arylalkyl urethane)$_{1-100}$, ($C_{5-50}$ alkyl urea)$_{1-100}$, ($C_{14-60}$ aryl urea)$_{1-100}$, ($C_{10-2000}$ alkylaryl urea)$_{1-100}$, ($C_{10-2000}$ arylalkyl urea)$_{1-100}$, ($C_{2-50}$ alkyl amide)$_{1-100}$, ($C_{7-60}$ aryl amide)$_{1-100}$, ($C_{8-2000}$ alkylaryl amide)$_{1-100}$, ($C_{8-2000}$ arylalkyl amide)$_{1-100}$, ($C_{3-30}$ alkyl anhydride)$_{1-100}$, ($C_{8-50}$ aryl anhydride)$_{1-100}$, ($C_{9-2000}$ alkylaryl anhydride)$_{1-100}$, ($C_{9-2000}$ arylalkyl anhydride)$_{1-100}$, ($C_{2-30}$ alkyl carbonate)$_{1-100}$, ($C_{7-50}$ aryl carbonate)$_{1-100}$, ($C_{8-2000}$ alkylaryl carbonate)$_{1-100}$, ($C_{8-2000}$ arylalkyl carbonate)$_{1-100}$, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$—CO—NH—($R^b$ or Ar—$R^b$—Ar)—NH—CO—O—, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$—$R^c$—O—CO—NH—($R^b$ or Ar—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$, —$R^a$—NH—CO—NH—($R^b$ or Ar—$R^b$—Ar)—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$—CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$—$R^c$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$, or a bond; each Z, independently, is —G—D, wherein G is —$R^a$—, —$R^a$—Ar—, —Ar—$R^a$—, or —Ar—; and D is —H, —OH, —SH, —$NH_2$, —NHOH, —$SO_3$H, —$OSO_3$H, —$CO_2$H, —$CONH_2$, —$CONHNH_2$, —CH($NH_2$)—$CO_2$H, —NH—$CH_2$—$CO_2$H, —P(OH)$_3$, —PO(OH)$_2$, —O—PO(OH)$_2$, —O—PO(OH)—O—PO(OH)$_2$, —O—PO($O^-$)—O—$CH_2CH_2NH_3^+$, —O—PO $(O^-)$—O—$CH_2CH_2$—$N^+(CH_3)_3$, -glycoside, -oligosaccharide, —CO-glycoside, —CO-oligosaccharide, —$OCH_3$, —$OCH_2(CHOH)_4$—$CH_2OH$, —$OCH_2(CHOH)_2$—$CH_2OH$, —CO—$OCH_2(CHOH)_4$—$CH_2OH$, —$C_6H_3$ $(OH)_2$, —$N(CH_2CO_2H)_2$, —CO—$N(CH_2CO_2H)_3$, —CO—NH—$C(CH_2CH_2CO_2H)_3$, —CO—NH—$C(CH_2CH_2OH)_3$, —$[CH_2$—$CH(CO_2R^a)]_{1-100}$—H, —$NH_3^+$, $N^+H_2R^a$, —$N^+HR^aR^b$, or —$N^+R^aR^bR^c$. Each of $R^a$, $R^b$, and $R^c$, independently, is $C_{1-20}$ alkyl and Ar is aryl. q is 0–30, and m is 0–30. Note that the sum of q and m is 0–30. Each of $R^1$ and $R^4$, independently, is =O or $C_{1-20}$ hydrocarbon. A hydrocarbon is a moiety containing carbon and hydrogen, e.g., alkyl, alkenyl, or alkynyl. Each of $R^2$ and $R^5$, independently, is $C_{1-20}$ hydrocarbon; wherein $R^1$ and $R^2$, or $R^4$ and $R^5$ can join together to form $C_{6-40}$ aryl which is optionally substituted with halide, —OH, —$NHNH_2$, —$NH_2OH$, —NH—$CH_2$—$CO_2H$, —$CH_2$—$CH_2$—D, —$CH_2$—B—Z, —CO—$CH_2$—D, —CO—B—Z, —O—B—Z, or —NH—B—Z. Each of $R^3$ and $R^6$, independently, is —H, —$CH_2$—D, —B—Z, —G—E, —G—CO—E, or a side chain of an amino acid. E is $E_1$, $E_2$, or $E_3$, in which $E_1$ is $Y_1,Y_2$-amino, $(Y_1,Y_2$-alkyl)-amino, $Y_1,Y_2$-ethylenediamino, (dihydroxymethyl)alkylamino, $(X_1,X_3$-aryl)amino, or $X_1,X_3$-aryloxy; $E_2$ is $Y_1,Y_2$-alkoxy, $(Y_1,Y_2$-amino)alkoxy, $(Y_1,Y_2,Y_3$-aryl)oxy, (dihydroxyalkyl)-aryloxy, $(Y_1,Y_2,Y_3$-alkyl)amino, $(Y_1,Y_2,Y_3$-aryl)amino, dihydroxyalkylamino, $Y_1,Y_2,Y_3$-alkoxy, (trihydroxyalkyl)alkoxy, (trihydroxyalkyl)alkylamino, (dicarboxyalkyl)amino, $(Y_1,Y_2,Y_3$-alkyl)thio, $(X_1,X_3$-aryl)thio, $(Y_1,Y_2$-alkyl)thio, (dihydroxyalkyl)thio, $Y_1,Y_2$-dioxoalkyl, or tri-$(Y_1,Y_2,Y_3$-methylaminocarboxyethyl)methylamino; and $E_3$ is ((glycosidyl)oxoheteroaryl)amino, ((glycosidyl)oxoaryl)amino, $(X_1,X_2,X_3$-heteroaryl)amino, $(X_1$-diarylketone)amino, $(X,X_1$-oxoaryl)amino, $(X,X_1$-dioxoaryl)amino, $(Y_1$-alkyl,$Y_2$-alkyldioxoheteroaryl)amino, $(Y_1$-alkyl,$Y_2$-alkyldioxoaryl)amino, (di($Y_1,Y_2$-methyl)dioxoheteroaryl)amino, (di($Y_1,Y_2$-methyl)dioxoaryl)amino, ((glycosidyl)heteroaryl)amino, ((glycosidyl)aryl)amino, ((carboxylacetylalkyl)oxo-heteroaryl)amino, ((carboxylacetylalkyl)oxoaryl)amino, ((isopropylamino-hydroxyalkoxy)aryl)amino, $(X_1,X_2,X_3$-alkylaryl)amino, $(X_1,X_2,X_3$-heteroaryl)oxy, (isopropylaminohydroxyalkyl)aryloxy, $(X_1,X_2,X_3$-oxoheteroaryl)oxy, $(X_1,X_2,X_3$-oxoaryl)oxy, $(X_1,Y_1$-oxoheteroaryl)oxy, $(X_1$-diarylketone)oxy, $(X,X_1$-oxoaryl)oxy, $(X_1,X_2$-dioxoaryl)oxy, $(Y_1,Y_2$,di-aminodihydroxy)alkyl, $(X_1,X_2$-heteroaryl)thio, ((tricarboxylalkyl)ethylenediamino)alkoxy, $(X_1,X_2$-oxoaryl)thio, $(X_1,X_2$-dioxoaryl)thio, (glycosidylheteroaryl)thio, (glycosidylaryl)thio, $Y_1$-alkyl(thiocarbonyl)thio, $Y_1,Y_2$-alkyl(thiocarbonyl)thio, $Y_1,Y_2,Y_3$-alkyl(thiocarbonyl)thio, $(Y_1,Y_2$-aminothiocarbonyl)thio, (pyranosyl)thio, cysteinyl, tyrosinyl, (phenylalainyl)amino, (dicarboxyalkyl)thio, (aminoaryl)$_{1-100}$amino, (pyranosyl)amino, $(Y_1$-aminoaryl)$_{1-100}$ amino, (amino(sulfoaryl))$_{1-100}$amino, peptidyl, thymidinyl, uridinyl, guanosinyl, adenosinyl, cholesteryl, or biotinylalkoxy. X is halide. Each of $X_1$, $X_2$, and $X_3$, independently, is —$Y_1$, —O—$Y_1$, —S—$Y_1$, —NH—$Y_1$, —CO—O—$Y_1$, —O—CO—$Y_1$, —CO—NH—$Y_1$, —CO—$NY_1Y_2$, —NH—CO—$Y_1$, —$SO_2$—$Y_1$, —$CHY_1Y_2$, or —$NY_1Y_2$. Each of $Y_1$, $Y_2$, and $Y_3$, independently, is —Z or —B—Z. $R^N$ is H; or one of $R^3$ and $R^6$, together with $R^N$ is a bond and the other of $R^3$ and $R^6$ is as defined above. Each of x and y, independently, is 0 or 1; and s is 1–6Note that when x is 0, is =O; that when y is 0, $R^4$ is =O; that when x is 1, $R^1$ and $R^2$ join together to form $C_{6-40}$ aryl; and that when y is 1, $R^4$ and $R^5$ join together to form $C_{6-40}$ aryl.

Another aspect of this invention relates to a method for preparing a compound of formula (I-A).

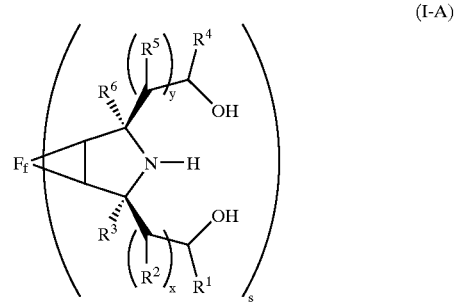

(I-A)

The method includes reacting a compound of formula (II):

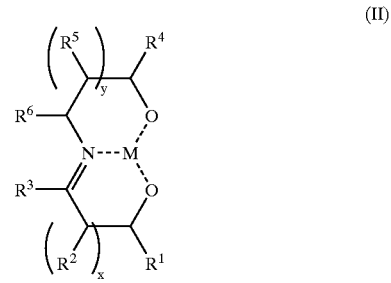

(II)

wherein M is a Cu, Mn, Fe, Co, Ni, Ru, Rh, Os, Zn, Cr, Ti, or Zr ion, with a fullerene compound $F_f$ of the formula $F(—K)_m(—Y—Z)_q$ wherein the sum of q and m is 0 to form a compound of formula (III):

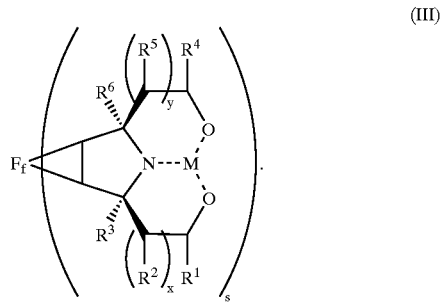

(III)

M is then removed from a compound of formula (III), e.g., by using an ion exchange resin such as Dowex, to form a compound of formula (I) wherein the sum of q and m is 0. The compound of formula (I) wherein the sum of q and m is 0 can be further treated with a nitrating or sulfating agent to form a nitrofullerene or cyclosulfated fullerene, and contacting the nitrofullerene or cyclosulfated fullerene with a nucleophilic agent to form a compound of formula (I) wherein the sum of q and m is greater than 0, i.e., a derivatized fulleropyrrolidine compound of this invention.

The compound of formula (II) can be prepared by reacting a compound of formula (IV):

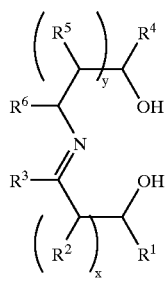

(IV)

with a metal salt MX, wherein M is a Cu, Mn, Fe, Co, Ni, Ru, Rh, Os, Zn, Cr, Ti, or Zr ion, and X is an anion such as sulfate, halide, acetate, and nitrate. As to the compound of formula (IV), it is prepared by reacting a compound of formula (V):

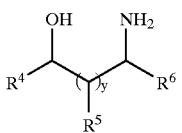

(V)

with a compound of formula (VI):

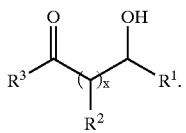

(VI)

Yet another aspect of this invention relates to a compound of formula (VII).

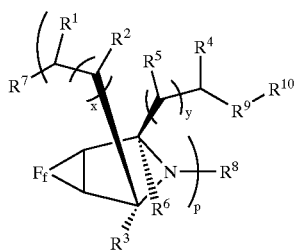

(VII)

$F_f$ is $F(-K)_m(-Y-Z)_q$ F is a fullerene core. Each K, independently, is —OH, —SH, —$NH_2$, —NHOH, —$SO_3H$, —$OSO_3H$, —$CO_2H$, —$CONH_2$, —$CONHNH_2$, —$P(OH)_3$, —$PO(OH)_2$, —O—$PO(OH)_2$, —O—PO(OH)—O—PO$(OH)_2$, —O—PO($O^-$)—O—$CH_2CH_2$—$NH_3^+$, —O—PO$(O^-)$—O—$CH_2CH_2$—$N^+(CH_3)_3$, -glycoside, —$OCH_3$, —$OCH_2(CHOH)_4$—$CH_2OH$, —$OCH_2(CHOH)_2$—$CH_2OH$, —NH—$CH_2$—$CO_2H$, —[CH($CO_2H$)—$CH_2$]$_{1-100}$—OH, —[CH($CO_2R^a$)—$CH_2$]$_{1-100}$—OH, —[C($CH_3$)($CO_2H$)—$CH_2$]$_{1-100}$—OH, —[C($CH_3$)($CO_2R^a$)—$CH_2$]$_{1-100}$—OH, —$N(OH)_2$, —$NH_3^+$, —$N^+H_2R^a$, —$N^+HR^aR^b$, or —$N^+R^aR^bR^c$. Each Y is —A—B—in which A is —O—, —NH—, —S—, —CO—O—, —O—CO—, —O—CO—O—, —O—CO—NH—, —NH—CO—NH—, —CO—NH—, or —NH—CO—; and B is —$R^a$—O—[Si($CH_3$)$_2$—O—]$_{1-100}$, $C_{1-2000}$ alkyl, $C_{6-40}$ aryl, $C_{7-2000}$ alkylaryl, $C_{7-2000}$ arylalkyl, ($C_{1-30}$ alkyl ether)$_{1-100}$, ($C_{6-40}$ aryl ether)$_{1-100}$, ($C_{7-2000}$ alkylaryl ether)$_{1-100}$, ($C_{7-2000}$ arylalkyl ether)$_{1-100}$, ($C_{1-30}$ alkyl thioether)$_{1-100}$, ($C_{6-40}$ aryl thioether)$_{1-100}$, ($C_{7-2000}$ alkylaryl thioether)$_{1-100}$, ($C_{7-2000}$ arylalkyl thioether)$_{1-100}$, ($C_{2-50}$ alkyl ester)$_{1-100}$, ($C_{7-2000}$ aryl ester)$_{1-100}$, ($C_{8-2000}$ alkylaryl ester)$_{1-100}$, ($C_{8-2000}$ arylalkyl ester)$_{1-100}$, —$R^a$—CO—O—($C_{1-30}$ alkyl ether)$_{1-100}$, —$R^a$—CO—O—($C_{6-40}$ aryl ether)$_{1-100}$, —CO—O—($C_{7-2000}$ alkylaryl ether)$_{1-100}$, —$R^a$—CO—O—($C_{7-2000}$ arylalkyl ether)$_{1-100}$, ($C_{4-50}$ alkyl urethane)$_{1-100}$, ($C_{14-60}$ aryl urethane)$_{1-100}$, ($C_{10-2000}$ alkylaryl urethane)$_{1-100}$, ($C_{10-2000}$ arylalkyl urethane)$_{1-100}$, ($C_{5-50}$ alkyl urea)$_{1-100}$, ($C_{14-60}$ aryl urea)$_{1-100}$, ($C_{10-2000}$ alkylaryl urea)$_{1-100}$, ($C_{10-2000}$ arylalkyl urea)$_{1-100}$, ($C_{2-50}$ alkyl amide)$_{1-100}$, ($C_{7-60}$ aryl amide)$_{1-100}$, ($C_{8-2000}$ alkylaryl amide)$_{1-100}$, ($C_{8-2000}$ arylalkyl amide)$_{1-100}$, ($C_{3-30}$ alkyl anhydride)$_{1-100}$, ($C_{8-50}$ aryl anhydride)$_{1-100}$, ($C_{9-2000}$ alkylaryl anhydride)$_{1-100}$, ($C_{9-2000}$ arylalkyl anhydride)$_{1-100}$, ($C_{2-30}$ alkyl carbonate)$_{1-100}$, ($C_{7-50}$ aryl carbonate)$_{1-100}$, ($C_{8-2000}$ alkylaryl carbonate)$_{1-100}$, ($C_{8-2000}$ arylalkyl carbonate)$_{1-100}$, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$—CO—NH—($R^b$ or Ar—$R^b$—Ar)—NH—CO—O—, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$—$R^c$—O—CO—NH—($R^b$ or Ar—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$, —$R^a$—NH—CO—NH—($R^b$ or Ar—$R^b$—Ar)—NH—CO—($C_{2-50}$ alkyl ester, $C_{7-60}$ aryl ester, $C_{8-2000}$ alkylaryl ester, or $C_{8-2000}$ arylalkyl ester)$_{1-100}$, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$—CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$—$R^c$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$, or a bond; each Z, independently, is —G—D, wherein G is —$R^a$—, —$R^a$—Ar—, —Ar—$R^a$—, or —Ar—; and D is —H, —OH, —SH, —$NH_2$, —NHOH, —$SO_3H$, —$OSO_3H$, —$CO_2H$, —$CONH_2$, —$CONHNH_2$, —CH($NH_2$)—$CO_2H$, —NH—$CH_2$—$CO_2H$, —$P(OH)_3$, —$PO(OH)_2$, —O—$PO(OH)_2$, —O—PO(OH)—O—PO$(OH)_2$, —O—PO($O^-$)—O—$CH_2CH_2NH_3^+$, —O—PO$(O^-)$—O—$CH_2CH_2$—$N^+(CH_3)_3$, -glycoside, -oligosaccharide, —CO-glycoside, —CO-oligosaccharide, —$OCH_3$, —$OCH_2(CHOH)_4$—$CH_2OH$, —$OCH_2(CHOH)_2$—$CH_2OH$, —CO—$OCH_2(CHOH)_4$—$CH_2OH$, —$C_6H_3(OH)_2$, —$N(CH_2CO_2H)_2$, —CO—N$(CH_2CO_2H)_2$, —CO—NH—C($CH_2CO_2H)_3$, —CO—NH—C($CH_2CH_2OH)_3$, —[$CH_2$—CH($CO_2R^a$)]$_{1-100}$—H, —$NH_3^+$, $N^+H_2R^a$, —$N^+HR^aR^b$, or —$N^+R^aR^bR^c$. Each of $R^a$, $R^b$, and $R^c$, independently, is $C_{1-20}$ alkyl and Ar is aryl. q is 0–30, and m is 0–30. Note that the sum of q and m is 0–30. Each of $R^1$ and $R^4$, independently, is =O or $C_{1-20}$ hydrocarbon. Each of $R^2$ and $R^5$, independently, is $C_{1-20}$ hydrocarbon. $R^1$ and $R^2$, or $R^4$ and $R^5$ can join together to form $C_{6-40}$ aryl which is optionally substituted with halide, —OH, —NHNH$_2$, —NH$_2$OH, —NH—CH$_2$—CO$_2$H, —CH$_2$—CH$_2$—D, —CH$_2$—B—Z, —CO—CH$_2$—D, —CO—B—Z, —O—B—Z, or —NH—B—Z. Each of $R^3$ and $R^6$, independently, is —H, —CH$_2$—D, —B—Z, —G—E, —G—CO—E or a side chain of an amino acid. Each of B, D, and Z having been defined above. E is $E_1$, $E_2$, or $E_3$, in which $E_1$ is $Y_1,Y_2$-amino, $(Y_1,Y_2$-alkyl)-amino, $Y_1,Y_2$-ethylenediamino, (dihydroxymethyl)alkylamino, $(X_1,X_3$-aryl)amino, or $X_1,X_3$-aryloxy; $E_2$ is $Y_1,Y_2$-alkoxy, $(Y_1,Y_2$-amino)alkoxy, $(Y_1,Y_2,Y_3$-aryl)oxy, (dihydroxyalkyl)-aryloxy, $(Y_1,Y_2,Y_3$-alkyl)amino, $(Y_1,Y_2,Y_3$-aryl)amino, dihydroxyalkylamino, $Y_1,Y_2,Y_3$-alkoxy, (trihydroxyalkyl)alkoxy, (trihydroxyalkyl)-alkylamino, (dicarboxyalkyl)amino, $(Y_1,Y_2,Y_3$-alkyl)thio, $(X_1,X_3$-aryl)thio, $(Y_1,Y_2$-alkyl)thio, (dihydroxyalkyl)thio, $Y_1,Y_2$-dioxoalkyl, or tri-$(Y_1,Y_2,Y_3$-methylaminocarboxyethyl) methylamino; and $E_3$ is ((glycosidyl)oxoheteroaryl)amino, ((glycosidyl)oxoaryl)amino, $(X_1,X_2,X_3$-heteroaryl)amino, $(X_1$-diarylketone)amino, $(X,X_1$-oxoaryl)amino, $(X,X_1$-dioxoaryl)amino, $(Y_1$-alkyl,$Y_2$-alkyldioxoheteroaryl)amino, $(Y_1$-alkyl,$Y_2$-alkyldioxoaryl)amino, $(di(Y_1,Y_2$-methyl) dioxoheteroaryl)amino, $(di(Y_1,Y_2$-methyl)dioxoaryl)amino, ((glycosidyl)heteroaryl)amino, ((glycosidyl)aryl)amino, ((carboxylacetylalkyl)oxo-heteroaryl)amino, ((carboxylacetylalkyl)oxoaryl)amino, ((isopropylamino-hydroxy-alkoxy)aryl)amino, $(X_1,X_2,X_3$-alkylaryl)amino, $(X_1,X_2,X_3$-heteroaryl)oxy, (isopropylaminohydroxyalkyl)aryloxy, $(X_1,X_2,X_3$-oxoheteroaryl)oxy, $(X_1,X_2,X_3$-oxoaryl)oxy, $(X_1,Y_1$-oxoheteroaryl)oxy, $(X_1$-diarylketone)oxy, $(X,X_1$-oxoaryl)oxy, $(X_1,X_2$-dioxoaryl)oxy, $(Y_1,Y_2$-diaminodihydroxy)alkyl, $(X_1,X_2$-heteroaryl)thio, ((tricarboxylalkyl)ethylene-diamino)alkoxy, $(X_1,X_2$-oxoaryl)thio, $(X_1,X_2$-dioxoaryl)thio, (glycosidylheteroaryl)thio, (glycosidylaryl)thio, $Y_1$-alkyl(thiocarbonyl)thio, $Y_1,Y_2$-alkyl(thiocarbonyl)thio, $Y_1,Y_2,Y_3$-alkyl(thiocarbonyl)thio, $(Y_1,Y_2$-aminothiocarbonyl)thio, (pyranosyl)thio, cysteinyl, tyrosinyl, (phenylalainyl)amino, (dicarboxyalkyl)thio, (aminoaryl)$_{1-100}$amino, (pyranosyl)amino, $(Y_1$-aminoaryl)$_{1-100}$amino, (amino(sulfoaryl))$_{1-100}$amino, peptidyl, thymidinyl, uridinyl, guanosinyl, adenosinyl, cholesteryl, or biotinylalkoxy. X is halide. Each of $X_1$, $X_2$, and $X_3$, independently, is —$Y_1$, —O—$Y_1$, —S—$Y_1$, —NH—$Y_1$, —CO—O—$Y_1$, —O—CO—$Y_1$, —CO—NH—$Y_1$, —CO—N$Y_1Y_2$, —NH—CO—$Y_1$, —SO$_2$—$Y_1$, —CH$Y_1Y_2$, or —N$Y_1Y_2$. Each of $Y_1$, $Y_2$, and $Y_3$, independently, is —Z or —B—Z. $R^7$ is —$R^d$ or O—$R^e$. $R^d$ is —OH, —OM, —NHNH$_2$, —NHOH, —NH—CH$_2$—CO$_2$H, —O—B—Z, —NH—B—Z, —E, —O—G—E, —NH—G—E, —O—G—CO—E, or —NH—G—CO—E. M is Cu, Mn, Fe, Co, Ni, Ru, Rh, Os, Zn, Cr, Ti, or Zr ion. $R^e$ is —H, —CH$_2$—CH$_2$—D, —CH$_2$—B—Z, —CH$_2$—G—E, —CH$_2$—G—CO—E, —CO—CH$_2$—D, —CO—B—Z, —CO—G—E, or —CO—G—CO—E. $R^8$ is $R^e$. $R^9$ is —O— or a bond. $R^{10}$ is —$R^d$ or —$R^e$. Each of x and y, independently, is 0 or 1; and p is 1–30. Note that when x is 0, $R^1$ is =O, and $R^7$ is —$R^d$; that when y is 0, $R^4$ is =O, and $R^9$ is a bond, and $R^{10}$ is —$R^d$; that when x is 1, $R^1$ and $R^2$ join together to form $C_{6-40}$ aryl, and $R^7$ is —O—$R^e$; and that when y is 1, $R^4$ and $R^5$ join together to form $C_{6-40}$ aryl, $R^9$ is —O—, and $R^{10}$ is —$R^e$. In addition, when p is greater than 1, x is 0.

Still another aspect of this invention relates to a compound of formula (VIII):

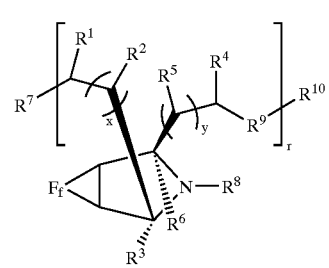

(VIII)

$F_f$ is F(—K)$_m$(—Y—Z)$_q$. F is a fullerene core. Each K, independently, is —OH, —SH, —NH$_2$, —NHOH, —SO$_3$H, —OSO$_3$H, —CO$_2$H, —CONH$_2$, —CONHNH$_2$, —P(OH)$_3$, —PO(OH)$_2$, —O—PO(OH)$_2$, —O—PO(OH)—O—PO(OH)$_2$, —O—PO(O$^-$)—O—CH$_2$CH$_2$—NH$_3^+$, —O—PO(O$^-$)—O—CH$_2$CH$_2$—N+(CH$_3$)$_3$, -glycoside, —OCH$_3$, —OCH$_2$(CHOH)$_4$—CH$_2$OH, —OCH$_2$(CHOH)$_2$—CH$_2$OH, —NH—CH$_2$—CO$_2$H, —[CH(CO$_2$H)—CH$_2$]$_{1-100}$—OH, —[CH(CO$_2$R$^a$)—CH$_2$]$_{1-100}$—OH, —[C(CH$_3$)(CO$_2$H)—CH$_2$]$_{1-100}$—OH, —[C(CH$_3$)(CO$_2$R$^a$)—CH$_2$]$_{1-100}$—OH$_2$, —N(OH)$_2$, —NH$_3^+$, —N$^+$H$_2$R$^a$, —N$^+$HR$^a$R$^b$, or —N$^+$R$^a$R$^b$R$^c$; each Y is —A—B—, in which A is —O—, —NH—, —S—, —CO—O—, —O—CO—, —O—CO—O—, —O—CO—NH—, —NH—CO—NH—, —CO—NH—, or —NH—CO—. B is —R$^a$—O—[Si(CH$_3$)$_2$—O—]$_{1-100}$, $C_{1-2000}$ alkyl, $C_{6-40}$ aryl, $C_{7-2000}$ alkylaryl, $C_{7-2000}$ arylalkyl, ($C_{1-30}$ alkyl ether)$_{1-100}$, ($C_{6-40}$ aryl ether)$_{1-100}$, ($C_{7-2000}$ alkylaryl ether)$_{1-100}$, ($C_{7-2000}$ arylalkyl ether)$_{1-100}$, ($C_{1-30}$ alkyl thioether)$_{1-100}$, ($C_{6-40}$ aryl thioether)$_{1-100}$, ($C_{7-2000}$ alkylaryl thioether)$_{1-100}$, ($C_{7-2000}$ arylalkyl thioether)$_{1-100}$, ($C_{2-50}$ alkyl ester)$_{1-100}$, ($C_{7-2000}$ aryl ester)$_{1-100}$, ($C_{8-2000}$ alkylaryl ester)$_{1-100}$, ($C_{8-2000}$ arylalkyl ester)$_{1-100}$, —R$^a$—CO—O—($C_{1-30}$ alkyl ether)$_{1-100}$, —R$^a$—CO—O—($C_{6-40}$ aryl ether)$_{1-100}$, —R$^a$—CO—O—($C_{7-2000}$ alkylaryl ether)$_{1-100}$, —R$^a$—CO—O—($C_{7-2000}$ arylalkyl ether)$_{1-100}$, ($C_{4-50}$ alkyl urethane)$_{1-100}$, ($C_{14-60}$ aryl urethane)$_{1-100}$, ($C_{10-2000}$ alkylaryl urethane)$_{1-100}$, ($C_{10-2000}$ arylalkyl urethane)$_{1-100}$, ($C_{5-50}$ alkyl urea)$_{1-100}$, ($C_{14-60}$ aryl urea)$_{1-100}$, ($C_{10-2000}$ alkylaryl urea)$_{1-100}$, ($C_{10-2000}$ arylalkyl urea)$_{1-100}$, ($C_{2-50}$ alkyl amide)$_{1-100}$, ($C_{7-60}$ aryl amide)$_{1-100}$, ($C_{8-2000}$ alkylaryl amide)$_{1-100}$, ($C_{8-2000}$ arylalkyl amide)$_{1-100}$, ($C_{3-30}$ alkyl anhydride)$_{1-100}$, ($C_{8-50}$ aryl anhydride)$_{1-100}$, ($C_{9-2000}$ alkylaryl anhydride)$_{1-100}$, ($C_{9-2000}$ arylalkyl anhydride)$_{1-100}$, ($C_{2-30}$ alkyl carbonate)$_{1-100}$, ($C_{7-50}$ aryl carbonate)$_{1-100}$, ($C_{8-2000}$ alkylaryl carbonate)$_{1-100}$, ($C_{8-2000}$ arylalkyl carbonate)$_{1-100}$, —R$^a$—O—CO—NH—(R$^b$ or Ar—R$^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$, —R$^a$O—CO—NH—(R$^b$ or Ar—R$^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$, —R$^a$—O—CO—NH—(R$^b$ or Ar—R$^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$—CO—NH—(R$^b$ or Ar—R$^b$—Ar)—NH—CO—O—, —R$^a$—O—CO—NH—(R$^b$ or Ar—R$^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$—R$^c$—O—CO—NH—(R$^b$ or Ar—R$^b$—Ar)—NH—CO—O—, —R$^a$—NH—CO—NH—(R$^b$ or Ar—R$^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$, —R$^a$—NH—CO—NH—(R$^b$ or Ar—R$^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$, —R$^a$—NH—CO—NH—(R$^b$ or Ar—R$^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$—CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$—$R^c$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $Cg_{8-2000}$ alkylaryl amide, or $C_{8-2000}$ arylalkyl amide)$_{1-100}$, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$, or a bond. Each Z, independently, is —G—D, wherein G is —$R^a$—, —$R^a$—Ar—, —Ar—$R^a$—, or —Ar—; and D is —H, —OH, —SH, —NH$_2$, —NHOH, —SO$_3$H, —OSO$_3$H, —CO$_2$H, —CONH$_2$, —CONHNH$_2$, —CH(NH$_2$)—CO$_2$H, —NH—CH$_2$—CO$_2$H, —P(OH)$_3$, —PO(OH)$_2$, —O—PO(OH)$_2$, —O—PO(OH)—O—PO(OH)$_2$, —O—PO(O$^-$)—O—CH$_2$CH$_2$NH$_3$+, —O—PO(O$^-$)—O—CH$_2$CH$_2$—N$^+$(CH$_3$)$_3$, -glycoside, -oligosaccharide, —CO-glycoside, —CO-oligosaccharide, —OCH$_3$, —OCH$_2$(CHOH)$_4$—CH$_2$OH, —OCH$_2$(CHOH)$_2$—CH$_2$OH, —CO—OCH$_2$(CHOH)$_4$—CH$_2$OH, —C$_6$H$_3$(OH)$_2$, —N(CH$_2$CO$_2$H)$_2$, —CO—N(CH$_2$CO$_2$H)$_2$, —CO—NH—C(CH$_2$CH$_2$CO$_2$H)$_3$, —CO—NH—C(CH$_2$CH$_2$OH)$_3$, [CH$_2$—CH(CO$_2$R$^a$)]$_{1-100}$—H, —NH$_3$$^+$, —N$^+$H$_2$R$^a$, —N$^+$HR$^a$R$^b$, or —N$^+$R$^a$R$^b$R$^c$. Each of R$^a$, R$^b$, and R$^c$, independently, is $C_{1-20}$ alkyl and Ar is aryl. q is 0–30, and m is 0–30. Note that the sum of q and m is 0–30. Each of R$^1$ and R$^4$, independently, is =O or $C_{1-20}$ hydrocarbon; and each of R$^2$ and R$^5$, independently, is $C_{1-20}$ hydrocarbon. R$^1$ and R$^2$, or R$^4$ and R$^5$ can join together to form $C_{6-40}$ aryl which is optionally substituted with halide, —OH, —NHNH$_2$, —NH$_2$OH, —NH—CH$_2$—CO$_2$H, —CH$_2$—CH$_2$—D, —CH$_2$—B—Z, —CO—CH$_2$—D, —CO—B—Z, —O—B—Z, or —NH—B—Z. Each of R$^3$ and R$^6$, independently, is —H, —CH$_2$—D, —B—Z, —G—E, —G—CO—E or a side chain of an amino acid. E is E$_1$, E$_2$, or E$_3$, in which E$_1$ is Y$_1$,Y$_2$-amino, (Y$_1$,Y$_2$-alkyl)-amino, Y$_1$,Y$_2$-ethylenediamino, (dihydroxymethyl)alkylamino, (X$_1$,X$_3$-aryl)amino, or X$_1$,X$_3$-aryloxy; E$_2$ is Y$_1$,Y$_2$-alkoxy, (Y$_1$,Y$_2$-amino)alkoxy, (Y$_1$,Y$_2$,Y$_3$-aryl)oxy, (dihydroxyalkyl)-aryloxy, (Y$_1$,Y$_2$,Y$_3$-alkyl)amino, (Y$_1$,Y$_2$,Y$_3$-aryl)amino, dihydroxyalkylamino, Y$_1$,Y$_2$,Y$_3$-alkoxy, (trihydroxyalkyl)alkoxy, (trihydroxyalkyl)alkylamino, (dicarboxyalkyl)amino, (Y$_1$,Y$_2$,Y$_3$-alkyl)thio, (X$_1$,X$_3$-aryl)thio, (Y$_1$,Y$_2$-alkyl)thio, (dihydroxyalkyl)thio, Y$_1$,Y$_2$-dioxoalkyl, or tri-(Y$_1$,Y$_2$,Y$_3$-methylaminocarboxyethyl)methylamino; and E$_3$ is ((glycosidyl)oxoheteroaryl)amino, ((glycosidyl)oxoaryl)amino, (X$_1$,X$_2$,X$_3$-heteroaryl)amino, (X$_1$-diarylketone)amino, (X,X$_1$-oxoaryl)amino, (X,X$_1$-dioxoaryl)amino, (Y$_1$-alkyl,Y$_2$-alkyldioxoheteroaryl)amino, (Y$_1$-alkyl,Y$_2$-alkyldioxoaryl)amino, (di(Y$_1$,Y$_2$-methyl)dioxoheteroaryl)amino, (di(Y$_1$,Y$_2$-methyl)dioxoaryl)amino, ((glycosidyl)heteroaryl)amino, ((glycosidyl)aryl)amino, ((carboxylacetylalkyl)oxo-heteroaryl)amino, ((carboxylacetylalkyl)oxoaryl)amino, ((isopropylamino-hydroxy-alkoxy)aryl)amino, (X$_1$,X$_2$,X$_3$-alkylaryl)amino, (X$_1$,X$_2$,X$_3$-heteroaryl)oxy, (isopropylaminohydroxyalkyl)aryloxy, (X$_1$,X$_2$,X$_3$-oxoheteroaryl)oxy, (X$_1$,X$_2$,X$_3$-oxoaryl)oxy, (X$_1$,Y$_1$-oxoheteroaryl)oxy, (X$_1$-diarylketone)oxy, (X,X$_1$-oxoaryl)oxy, (X$_1$,X$_2$-dioxoaryl)oxy, (Y$_1$,Y$_2$-diaminodihydroxy)alkyl, (X$_1$,X$_2$-heteroaryl)thio, ((tricarboxylalkyl)ethylene-diamino)alkoxy, (X$_1$,X$_2$-oxoaryl)thio, (X$_1$,X$_2$-dioxoaryl)thio, (glycosidylheteroaryl)thio, (glycosidylaryl)thio, Y$_1$-alkyl(thiocarbonyl)thio, Y$_1$,Y$_2$-alkyl(thiocarbonyl)thio, Y$_1$,Y$_2$,Y$_3$-alkyl(thiocarbonyl)thio, (Y$_1$,Y$_2$-aminothiocarbonyl)thio, (pyranosyl)thio, cysteinyl, tyrosinyl, (phenylalainyl)amino, (dicarboxyalkyl)thio, (aminoaryl)$_{1-100}$amino, (pyranosyl)amino, (Y$_1$-aminoaryl)$_{1-100}$amino, (amino(sulfoaryl))$_{1-100}$amino, peptidyl, thymidinyl, uridinyl, guanosinyl, adenosinyl, cholesteryl, or biotinylalkoxy. X is halide. Each of X$_1$, X$_2$, and X$_3$, independently, is —Y$_1$, —O—Y$_1$, —S—Y$_1$, —NH—Y$_1$, —CO—O—Y$_1$, —O—CO—Y$_1$, —CO—NH—Y$_1$, —CO—NY$_1$Y$_2$, —NH—CO—Y$_1$, —SO$_2$—Y$_1$, —CHY$_1$Y$_2$, or —NY$_1$Y$_2$. Each of Y$_1$,Y$_2$, and Y$_3$, independently, is —Z or —B—Z. R$^7$ is —R$^d$ or —O—R$^e$. R$^d$ is —OH, —OM, —NHNH$_2$, —NHOH, —NH—CH$_2$—CO$_2$H, —O—B—Z, —NH—B—Z, —E, —O—G—E, —NH—G—E, —O—G—CO—E, or —NH—G—CO—E. M is Cu, Mn, Fe, Co, Ni, Ru, Rh, Os, Zn, Cr, Ti, or Zr ion. R$^e$ is —H, —CH$_2$—CH$_2$—D, —CH$_2$—B—Z, —CH$_2$—G—E, —CH$_2$—G—CO—E, —CO—CH$_2$—D, —CO—B—Z, —CO—G—E, or —CO—G—CO—E. R$^8$ is R$^e$. R$^9$ is —O—R$^f$— or —R$^g$—. R$^f$ is —CO—B—G—O—, —CO—B—G—NH—, —CO—B—G—CO—O—, or —CO—B—G—CO—NH—. R$^g$ is —NH—, —O—, —O—B—G—O—, —NH—B—G—O—, —NH—B—G—NH—, —O—CO—B—G—CO—O—, or —NH—CO—B—G—CO—NH—. R$^{10}$ is —H. Each of x and y, independently, is 0 or 1; and r is 1–100. Note that when x is 0, R$^1$ is =O, and R$^7$ is —R$^d$; that when y is 0, R$^4$ is =O, and R$^9$ is —R$^g$, and R$^{10}$ is —H; that when x is 1, R$^1$ and R$^2$ join together to form $C_{6-40}$ aryl, and R$^7$ is —O—R$^e$; and that when y is 1, R$^4$ and R$^5$ join together to form $C_{6-40}$ aryl, R$^9$ is —O—R$^f$, and R$^{10}$ is —H. Further, when r is greater than 1, x is 0.

A salt of a compound of the present invention is also within the scope of this invention. For example, a salt can form between an amino moiety and an anion such as sulfate, pyrosulfate bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, or maleate.

As used herein, a fullerene core is $C_{60}$, $C_{61}$, $C_{62}$, $C_{63}$, $C_{64}$, $C_{65}$, $C_{70}$, $C_{76}$, $C_{78}$, $C_{82}$, $C_{84}$, or $C_{92}$, or La@$C_n$, Ho@$C_n$, Gd@$C_n$, or Er@$C_n$, in which n is 60, 74, or 82.

An amino acid is a molecule containing both an amino group and a carboxylic acid, e.g., alanine, aspartic acid, cysteine, glutamic acid, phenylalanine, halophenylalanine, hydroxyphenylalanine, glycine, histidine, isoleucine, lysine, leucine, methionine, asparagine, glytamine, arginine, serine, theronine, valine, tryptophan, tyrosine, 2-aminobutyric acid, halophenylalanine, cyclohexylalanine, citrulline, homocitrulline, homoserine, norleucine, norvaline, or omithine. Side chain of an amino acid is the substituent that is bonded to the carbon atom adjacent to the carbonyl carbon, i.e., the α-carbon atom. For example, the side chain of each of alanine and ornithine is —CH$_3$ and —(CH$_2$)$_3$NH$_2$, respectively. A peptidyl is a peptide moiety containing 2–100 amino acid residues.

By the term "alkyl" is meant a straight chain that contains 1–30 carbon atoms, or a branched hydrocarbon chain of 3–30 carbon atoms, or cyclic hydrocarbon groups containing 3–30 carbon atoms, or otherwise indicated. These alkyl groups may also contain one or more double bond or triple bond and the cyclic alkyl groups may contain one or more heteroatoms, which are, typically, nitrogen, oxygen, or sulfur. Examples of alkyl groups include, but are not limited to, methyl, ethyl, propyl, isopropyl, butyl, isobutyl, tert-butyl, amyl, pentyl, hexyl, heptyl, octyl, nonyl, decyl, pentadecyl, icosyl, allyl, 2-butenyl, 2-pentenyl, 3-hexenyl, 4-decenyl, 5-nonadecenyl, 2-butnyl, 3-octnyl, 5-octadecnyl, cyclopropyl, cyclopentyl, cyclohexyl, cycloheptyl, adamantyl, norbornyl, isobornyl, cyclopentyl-methyl, cyclohexylmethyl, 1- or 2-cyclohexylethyl, cyclo-pentenyl, cyclohexenyl, cycloheptenyl, cyclo-octenyl, tetrahydrofuranyl, tetrahydropyranyl, piperidinyl, morpholino and pyrrolindinyl groups.

As used herein, the term "aryl" refers to $C_{6-40}$ aromatic rings. These moieties may also be fused rings and can be fused with aryl or heteroaryl which is as defined below. Fused rings are rings that share a common carbon-carbon bond. Typically aryl groups include phenyl, naphthyl, biphenyl, indazolyl, phenanthryl, and anthracyl.

By the term "heteroaryl" in this disclosure is meant $C_{6-40}$ aromatic rings that contain one or more heteroatoms as defined above. These moieties may also be fused rings. Examples of heteroaryl groups include pyridyl, pyrazinyl, pyrimidyl, furyl, pyrrolyl, thienyl, thiazolyl, oxazolyl, imidazolyl, coumarinyl, indolyl, benzofuranyl, benzthiazolyl, benzothienyl, and benzothiadiazolyl.

As used herein, the term "halide" is defined as fluoro, chloro, bromo, or iodo. The term "nucleophilic agent" is defined as an electron-rich species that donates electrons in a reaction. Examples of nucleophilic agents that can be employed in the preparation of derivatized fulleropyrrolidines include amine, phenol, alkoxide, organothiolate, carbanion, organoamide anion, thiol, amino acid, and thiol carbamate anion. Note that the just-mentioned nucleophilic agents can be unsubstituted or substituted with other functional groups. Examples of substituted nucleophilic agents include 1,4-naphthoquinonyl-amine, tyrosine, dihydroxypropylthiol, and the like.

The structures of many of the moieties mentioned above are shown below within the pair of parentheses following each of the moieties: alkyl ether (—R—O—), aryl ether (—Ar—O—), alkylaryl ether (—R—Ar—O—), arylalkyl ether (—Ar—R—O—), alkyl thioether (—R—S—), aryl thioether (—Ar—S—), alkylaryl thioether (—R—Ar—S—), arylalkyl thioether (—Ar—R—S—), alkyl ester (—R—O—CO—, —R—CO—O—, —R$_1$—CO—O—R$_2$—O—CO—, or —R$_1$—O—CO—R$_2$—CO—O—), aryl ester (—Ar—O—CO—, —Ar—CO—O, —Ar$_1$—CO—O—Ar$_2$—O—CO—, or —Ar$_1$—O—CO—Ar$_2$—CO—O—), alkylaryl ester (—R—Ar—O—CO— or —R—Ar—CO—O—), arylalkyl ester (—Ar—R—O—CO— or —Ar—R—CO—O—), alkyl urethane (—R$_1$—O—CO—NH—R$_2$—NH—CO—O—), aryl urethane (—Ar$_1$—O—CO—NH—Ar$_2$—NH—CO—O—), alkylaryl urethane (—R$_1$—Ar—O—CO—NH—R$_2$—NH—CO—O—, —R—Ar$_1$—O—CO—NH—Ar$_2$—NH—CO—O—, or —R$_1$—O—CO—NH—Ar—R$_2$—Ar—NH—CO—O—), arylalkyl urethane (—Ar—R$_1$—O—CO—NH—R$_2$—NH—CO—O—, —Ar$_1$—R—O—CO—NH—Ar$_2$—NH—CO—O—, or —Ar$_1$—O—CO—NH—Ar$_2$—R—Ar$_2$—NH—CO—O—), alkyl urea (—R$_1$—NH—CO—NH—R$_2$—NH—CO—NH—), aryl urea (—Ar$_1$—NH—CO—NH—Ar$_2$—NH—CO—NH—), alkylaryl urea (—R$_1$—Ar—NH—CO—NH—R$_2$—NH—CO—NH—, —R—Ar$_1$—NH—CO—NH—Ar$_2$—NH—CO—NH—, or —R$_1$—NH—CO—NH—Ar—R$_2$—Ar—NH—CO—NH—), arylalkyl urea (—Ar—R$_1$—NH—CO—NH—R$_2$—NH—CO—NH—, —Ar$_1$—R—NH—CO—NH—Ar$_2$—NH—CO—NH—, or —Ar$_1$—NH—CO—NH—Ar$_2$—R—Ar$_2$—NH—CO—NH—), alkyl amide (—R—NH—CO—, —R—CO—NH—, —R$_1$—CO—NH—R$_2$—NH—CO—, or —R$_1$—NH—CO—R$_2$—CO—NH—), aryl amide (—Ar—NH—CO—, —Ar—CO—NH—, —Ar$_1$—CO—NH—Ar$_2$—NH—CO—, or —Ar$_1$—NH—CO—Ar$_2$—CO—NH—), alkylaryl amide (—R—Ar—NH—CO—, —R—CO—NH—Ar—NH—CO—, or —R—NH—CO—Ar—CO—NH—), arylalkyl amide (—Ar—R—NH—CO—, —Ar—CO—NH—R—NH—CO—, or —Ar—NH—CO—R—CO—NH—), alkyl anhydride (—R—CO—O—CO—), aryl anhydride (—Ar—CO—O—CO—), alkylaryl anhydride (—R—Ar—CO—O—CO— or —R—CO—O—CO—Ar—CO—O—CO—), arylalkyl anhydride (—Ar—R—CO—O—CO— or —Ar—CO—O—CO—R—CO—O—CO—), alkyl carbonate (—R—O—CO—O—), aryl carbonate (—Ar—O—CO—O—), alkylaryl carbonate (—R—Ar—O—CO—O— or —R—O—CO—O—Ar—O—CO—O—), and arylalkyl carbonate (—Ar—R—O—CO—O— or —Ar—O—CO—O—R—O—CO—O—). Note that the di-substitution pattern on Ar can be para, meta, or ortho.

As will be discussed below, one can employ stereospecific compounds of this invention to treat patients suffering from cancer via photodynamic therapy. The stereospecific nature of these compounds allow specific interactions with many biologically active compounds, e.g., protein receptors. The compounds of this invention can also be used to develop chromatographic materials for purifying chiral molecules.

Other features and advantages of the present invention will be apparent from the following description of the preferred embodiments, and also from the appending claims.

DETAILED DESCRIPTION

The invention relates to sterospecific fullerene compounds, i.e., chiral (1-pyrrolino)fullerene derivatives, E-isomeric fulleropyrrolidine compounds, as well as polymers made of such E-isomeric compounds. Also disclosed are methods for preparing these E-isomeric compounds and E-isomeric fulleropyrrolidine polymers.

Methods of this invention allow an E-isomeric fulleropyrrolidine compound to be prepared directly, thereby obviating the need to purifying a racemic mixture of both E- and Z-isomers. Separation of optical isomers is generally very difficult due to the close physical properties of optical isomers. Specifically, the methods described herein utilize a key starting material, i.e., a bicyclic imine-containing organometallic compound such as N-pyruvylidenealaninatoaquocopper (II). This bicyclic imine-containing compound, which is formed of two difunctional compounds, effects a stereospecific cycloaddition reaction when reacts with a fullerene core, e.g., $C_{60}$, $C_{76}$, or Gd@$C_{82}$, thus forming only one fullerene isomer, i.e., the E-isomer.

Scheme I below illustrates a method for preparing an E-isomeric fulleropyrrolidine compound of this invention wherein its two carboxylic acid moieties are substituted at the same side of the pyrrolidine moiety. In the first step, an amino acid ($H_2N$—CH($R_b$)—COOH) and a pyruvic acid derivative ($R_b$—C(=O)—COOH) are used as exemplary difunctional compounds which react with each other to form a bicyclic imine-containing copper (II) complex in the presence of copper (II) acetate. See step (i). Note that the coordination of the two carboxylic acid moieties with the copper (II) ion restricts rotations of the N—C bond with respect to the N=C bond, thus forcing the two carboxylic acid to be at the same side of the pyrrolidine that is formed between the imine moiety, i.e., —C=N—C—, of the copper complex and a double bond of a fullerene core, e.g., $C_{60}$, via a cycloaddition reaction. See step (ii). Not only does the copper (II) ion enables only one stereospecific isomer, i.e., the E-isomer, to be formed, it also prevents thermal decarboxylation after dicarboxylic acid substituted fulleropyrrolidines are formed. By exchanging the copper (II) ion with the proton on a Dowex resin (H⁺ form), the corresponding E-isomeric dicarboxylic acid substituted fulleropyrrolidine product was isolated in a high yield (>85%). See Example 1 below.

Scheme II lies in that the former method employs a difunctional carboxylic acid, e.g., 2-ketoglutaric acid, whereas the latter method employs a difunctional phenol, e.g., salicylaldehyde. The difunctional phenol, e.g., a carbonyl-containing phenol, can then react with a difunctional carboxylic acid, e.g., an amino acid, in the presence of a metal

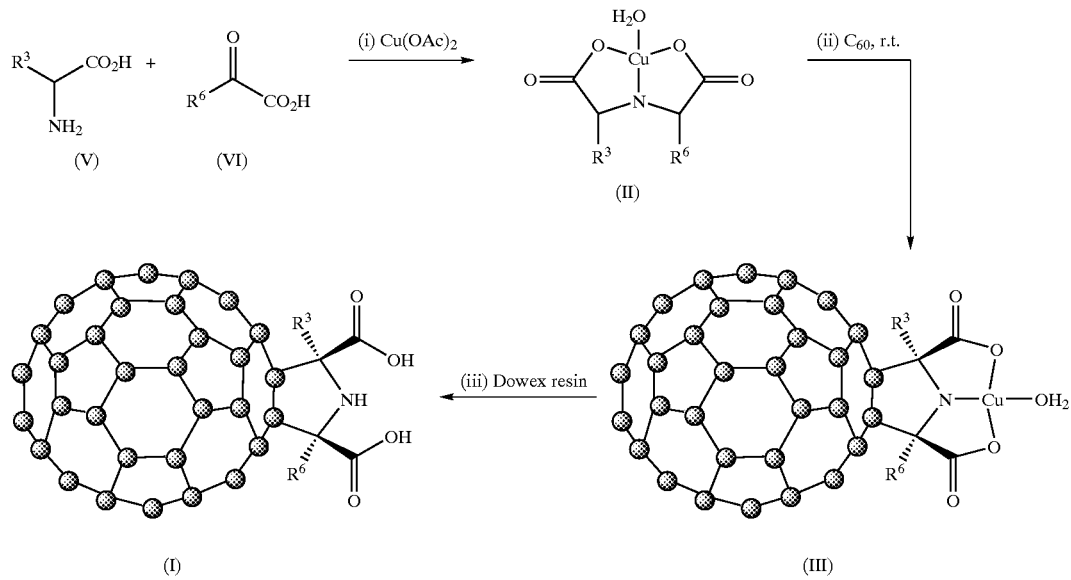

Scheme II below illustrates a method for preparing an E-isomeric fulleropyrrolidine compound of this invention wherein it is substituted with a carboxylic acid and an aromatic ring at the same side of the pyrrolidine moiety. The only difference between the methods shown in Scheme I and Scheme II lies in that the former method employs a difunctional carboxylic acid, e.g., 2-ketoglutaric acid, whereas the latter method employs a difunctional phenol, e.g., salicylaldehyde. The difunctional phenol, e.g., a carbonyl-containing phenol, can then react with a difunctional carboxylic acid, e.g., an amino acid, in the presence of a metal salt, e.g., $Cu(OAc)_2$ or $CoCl_2$, to form a bicyclic imine-containing metal complex. See step (i). The next two steps of the method, i.e., cycloaddition (step (ii)) and removal of metal ions (step (iii)), are identical to those described above. See Example 7 below.

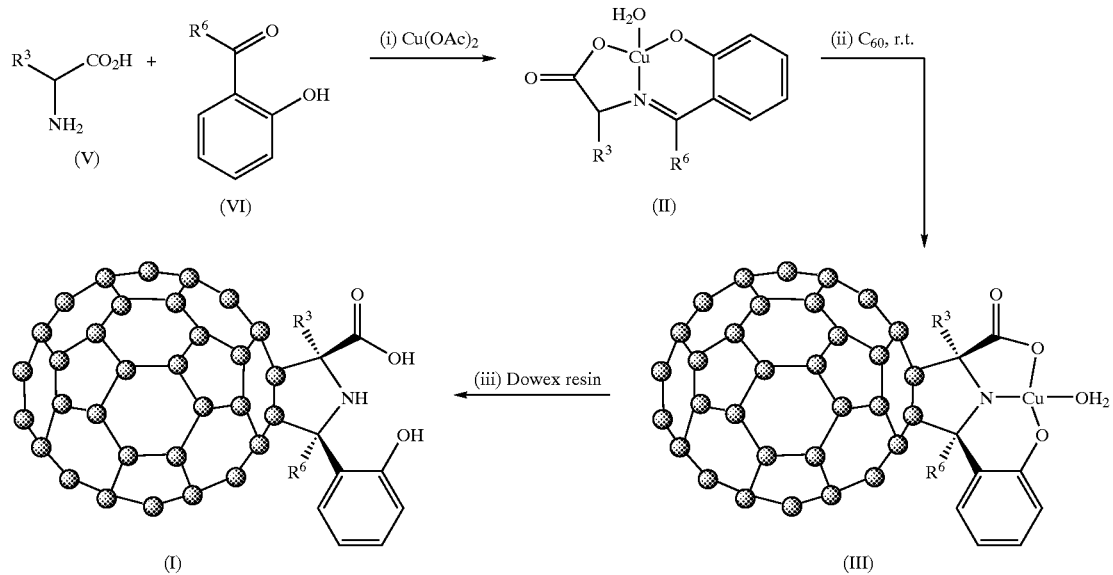

Alternatively, the bicyclic imine-containing organometallic compound can also be formed between an amine-containing phenol, e.g., 2'-aminoacetophenone, and a carbonyl-containing carboxylic acid, e.g., pyruvic acid, or a carbonyl-containing phenol, e.g., salicylaldehyde.

The resulting E-isomeric fulleropyrrolidine compound of formula (I) can be further derivatized, e.g., by attaching thereto a methylglucoside, by various known methods. See, e.g., U.S. Pat. No. 6,020,523. For example, the fulleropyrrolidine compound can be treated with a nitrating agent or a sulfating agent to form a nitrofulleropyrrolidine or a cyclosulfated fulleropyrrolidine intermediate, which can then be converted into a derivatized E-isomeric fulleropyrrolidine by reacting with a nucleophilic agent. Examples of a nitrating agent include sodium nitrite and concentrated $HNO_3$, dinitrogen tetraoxide, nitrogen dioxide, and fuming nitric acid. Cyclosulfated fullerene intermediates, on the other hand, can be formed by treating the fullerene with neat fuming sulfuric acid in the presence of an oxidant (e.g., $P_2O_5$, $V_2O_5$, or $SeO_2$). Examples of a nucleophilic agent include primary and secondary organoamino compound, alkoxide, organothiolate, organophenol compound, carbanion, organoamide anion, thiocarbamate ion, and the like.

Chiral (1-pyrrolino)fullerene derivatives can be prepared from the E-isomeric fulleropyrrolidine derivatives described herein. The 1-pyrroline double bond can be introduced, e.g., by oxidation of the pyrrolidine ring system. Other methods for generating the 1-pyrroline ring system are known in the art. For example, as shown in Scheme IV, a chiral (1-pyrroline)fullerene (4-B) can be obtained, e.g. from an E-isomeric fulleropyrrolidine, which is substituted with a carboxylic acid and an aromatic ring at the same side of the pyrrolidine moiety (4-A); the reaction delineated in Scheme IV can occur upon allowing (4-A) to stand in air.

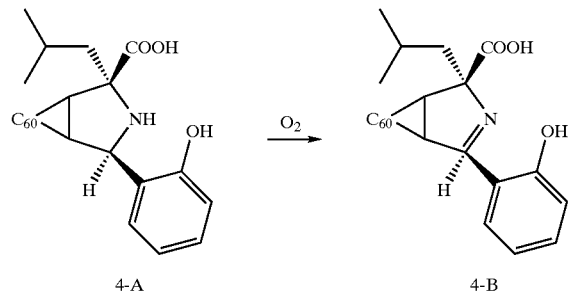

Scheme IV

While not wishing to be bound by any theory, it is believed that chiral (1-pyrrolino)fullerene derivatives, e.g., 4-B, can chelate metals, e.g., copper, through the nitrogen and the phenolic hydroxyl group. Thus, it is believed that these chiral (1-pyrrolino)fullerene derivatives can also function as ligands for reaction catalysts, e.g., catalysts for the oxidation of alcohols to aldehydes. Again, while not wishing to be bound by theory, it is believed that the electronegativity of the fullerene can result in a catalyst having a more highly electron deficient metal center relative to a comparable catalyst lacking the fullerene group. Again, still while not wishing to be bound by theory, it is believed that the steric properties of the fullerene can result in a catalyst exhibiting higher reaction stereoselectivity relative to a comparable catalyst lacking the fullerene group.

The E-isomeric fulleropyrrolidine compound of formula (I) can further react with each other to form a polymer (or an oligomer). The polymer formed can be a homopolymer or a copolymer, e.g., a random, a block, or a branched copolymer. Since a compound of formula (I) contains three termini, i.e., a pyrrolidine nitrogen ring atom and two carboxylic acid moieties (or a carboxylic moiety and a phenol hydroxy group, or two phenol hydroxyl groups), a number of polymers can be prepared via different linkages. Take a fulleropyrrolidine compound containing two carboxylic acid moieties as an example, a polymer can be formed by linking the N-terminus (i.e., the pyrrolidine nitrogen ring atom) of a first compound of formula (I) to the C-terminus (i.e., one of the two carboxylic acid moieties) of a second compound of formula (I), and the N-terminus of this second compound of formula (I) can in turn be linked to the C-terminus of a third compound of formula (I), and so on. This polymer design is similar to that of a peptide. The just-described polymer, i.e., a polymer of formula (VII), supra, can be prepared by forming an internal anhydride between the two carboxylic acid moieties, which is then treated with a base such as 1,8-diazabicyclo-[5.4.0]undec-7-ene (DBU) to effect the polymerization reaction. Due to the highly reactive nature of the anhydride moiety, derivatization of the fullerene should be done after the polymerization step. See Scheme III and Example 11 below.

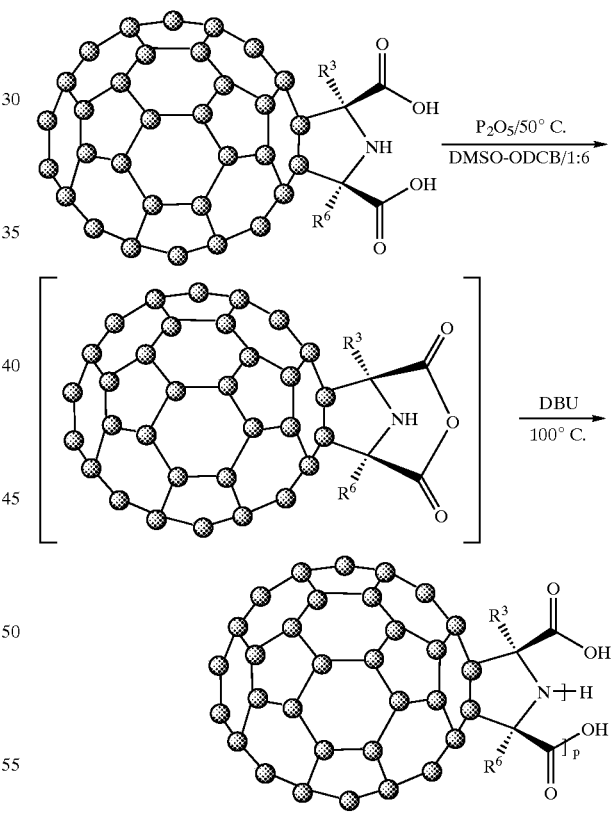

Scheme III

A polymer of formula (VII) can also be prepared using a fulleropyrrolidine compound having a phenol and a carboxylic acid moiety. Since this compound (or monomer) contains one carboxylic acid and one amino group, polymerization can be effected by using common peptide coupling reagents, e.g., dicyclohexylcarbodiimide (DCC), benzotriazol-1-yloxytris(dimethylamino)-phosphonium hexafluorophosphate (BOP), or O-benzo-triazol-1-yl-N,N, N',N'-tetramethyluronium hexafluorophosphate (HBTU).

Note that the hydroxy group of the phenol moiety may need to be protected, e.g., by silyl ethers, during polymerization.

Alternatively, a polymer of an E-isomeric fulleropyrrolidine compound of formula (I) can also be formed by linking the carboxylic acid moiety (or the hydroxy group of the phenol moiety) of one fulleropyrrolidine monomer to the carboxylic acid moiety of another fulleropyrrolidine monomer via a divalent linker, thus resulting in a polymer of formula (VIII). For example, a polyamide and a polyester can be formed by reacting a fulleropyrrolidine compound with two carboxylic acid moieties with a diamine (e.g., ethylenediamine) and a diol (e.g., 1,3-propanediol), respectively.

An E-isomeric fulleropyrrolidine compound of formula (I) can be used in photodynamic therapy (PDT) to treat patients suffering from cancer. See Example 16 below. The photo-induced cytotoxicity of a fullerene compound is connected with its ability to cleave DNA. Specifically, photo-generated triplet fullerene intermediate is involved in the energy transfer process which converts the ground-state triplet oxygen molecules into the excited molecular singlet oxygen $^1O_2$. Singlet oxygen is capable of inducing DNA damage and degeneration of other tissues that lead to mutagenic effects on biological cells. The stereospecific nature of an E-isomeric fulleropyrrolidine compound of formula (I) can enhance its affinity to DNA which is in the form of a double helix. Polymers of formulas (VII) and (VIII), which contain a plurality of fulleropyrrolidine compounds of formula (I), can further enhance its biological activities by allowing delivery of multiple fulleropyrrolidine compounds in a single molecule.

A pharmaceutical composition containing an effective amount of a fulleropyrrolidine compound of formula (I) (or a polymer formed therefrom) is also within the scope of this invention. The use of such a fulleropyrrolidine compound for the manufacture of a medicament for treating tumors is also within the scope of this invention. Still another aspect of this invention is a method for treating tumor by administering to a patient a pharmaceutical composition containing an effective amount of a fulleropyrrolidine compound of this invention. An effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, New York, 1970, 537. An effective amount of a pyridyl cyanoguanidine compound of this invention can range from about 1 mg/kg to about 150 mg/kg (e.g., about 1 mg/kg to about 100 mg/kg). Effective doses will also vary, as recognized by those skilled in the art, dependant on route of administration, excipient usage, and the possibility of co-usage with other therapeutic treatments including use of other antitumor agents and radiation therapy.

The pharmaceutical composition may be administered via the parenteral route, including orally, topically, subcutaneously, intraperitoneally, intramuscularly, and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds.

A fulleropyrrolidine compound of this invention can be formulated into dosage forms for other routes of administration utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of a pyridyl cyanoguanidine compound with a solid carrier and a lubricant. Examples of solid carriers include starch and sugar bentonite. The fulleropyrrolidine compound can also be administered in a form of a hard shell tablet or a capsule containing a binder, e.g., lactose or mannitol, a conventional filler, and a tableting agent.

Without further elaboration, it is believed that one skilled in the art can, based on the description herein, utilize the present invention to its fullest extent. The following specific examples are, therefore, to be construed as merely illustrative, and not limitative of the remainder of the disclosure in any way whatsoever. All publications recited herein, including patents, are hereby incorporated by reference in their entirety.

EXAMPLE 1

Synthesis of E-isomer of 1,3-dimethyl-fulleropyrrolidine-1, 3-dicarboxylic acid. In a conical flask charged with DL-alanine (2.25 g, 25 mmol) and a mixture of water and ethanol (20 ml, 2:1) and stirred for a period of 20 min was added pyruvic acid (2.2 g, 25 mmol). The reaction mixture was stirred at ambient temperature for 1.0 h. The resulting yellowish solution was then added copper (II) acetate (4.99 g, 25 mmol) in water-ethanol (20 ml) and stirred for an additional 24 h, causing precipitation of pale blue solids. The solids were filtered, washed with ethanol, and dried to yield N-pyruvylidenealaninatoaquocopper (II) complex.

To a solution of $C_{60}$ (350 mg, 0.49 mmol) in o-dichlorobenzene (140 ml), N-pyruvylidenealaninatoaquocopper (II) complex (0.34 g, 1.96 mmol, 4.0 equiv.) in pyridine (25 ml) was added via syringe under $N_2$. The solution mixture was stirred for a period of 15 h at ambient temperature. It was added hexane (100 ml) to effect precipitation of solid products. The solid precipitates were isolated by centrifuge, washed with hexane (50 ml), and dried in vaccuo. It was further washed twice by water, brine, and $CH_3CN$ (20 ml each) and dried in vaccuo to afford brown solids of 1,3-dimethyl-fulleropyrrolidine-1,3-dicarboxylatoaquocopper (II) complex (0.53 g). IR $\upsilon_{max}$ (KBr) 3424 (br, s), 1749 (w), 1716 (w), 1622 (s), 1385 (s), 1218 (w), 1182 (w), 1154 (w), 1070 (w), 751, 696, and 525.

Brown solids of 1,3-dimethyl-fulleropyrrolidine-1,3-dicarboxylatoaquocopper (II) complex (0.5 g) were dissolved in a mixture of pyridine (25 ml) and water (25 ml). It was stirred in the presence of Dowex acid resin (50WX8, 2.0 g) for a period of 2.0 h. The solid resin was filtered off. The remaining solution was stirred further with fresh Dowex acid resin (50WX8, 1.5 g) for an additional 30 min. At the end of the ion exchanging reaction, Dowex resin was filtered. After solvent evaporation of the filtrate, the resulting dark solids were washed with ethanol and dried in vaccuo to give the product of 1,3-dimethylfulleropyrrolidine-1,3-dicarboxylic acid (0.4 g). IR $\upsilon_{max}$ (KBr) 3422 (br, s), 3101 (w), 1779 (w), 1717, 1635 (s), 1488, 1388, 1242, 1162, 1036, 751, 681, and 526. Treatment of 1,3-dimethyl-fulleropyrrolidine-1,3-dicarboxylic acid with dil. HCl (2.0 N) gave the corresponding N-protonated 1,3-dimethyl-fulleropyrrolidine-1,3-dicarboxylic acid containing free carboxylic acids. IR $\upsilon_{max}$ (KBr) 3421 (br, s), 3245, 2930, 2859, 2575 (CO$_2$H), 1723 (s, CO$_2$H), 1641, 1453, 1414, 1169, 1111 (s), 955 (w), 801, 665 (w), 599 (w), and 470.

EXAMPLE 2

Synthesis of E-isomer of 1-dimethyl-3-hydroxyphenylmethyl-fulleropyrrolidine-1,3-dicarboxylic acid. In a conical flask charged with DL-tyrosine (4.52 g, 25 mmol) and a mixture of water and ethanol (20 ml, 2:1) and stirred for a period of 20 min was added pyruvic acid (2.2 g, 25 mmol). The reaction mixture was stirred at 50° C. for 2.0 h under basic condition at pH 810 using NaOH as a titration agent. The resulting yellowish solution was then added copper (II) chloride (3.4 g, 25 mmol) in water-ethanol (20 ml) and stirred for an additional 24 h, causing precipitation of pale blue solids. The solids were filtered, washed with water, ethanol, diethylether, and dried to yield N-pyruvylidenetyrosinatoaquocopper (II) complex. IR $\upsilon_{max}$ (KBr) 3490, 3371, 3290, 3151, 3052, 2971, 2932, 1613 (s), 1580, 1520, 1448, 1408, 1335, 1242, 1123, 1070, 891, 848, 810, 744, 705, 600, and 539.

Alternatively, in a conical flask charged with DL-alanine (2.27 g, 25 mmol) and a mixture of water and ethanol (20 ml, 2:1) and stirred for a period of 20 min was added p-hydroxyphenylpyruvic acid (4.5 g, 25 mmol). The reaction mixture was stirred at ambient temperature for 2.0 h. The resulting yellowish solution was then added copper (II) acetate (5.0 g, 25 mmol) in water-ethanol (20 ml) and stirred for an additional 24 h, causing precipitation of greenish blue solids. The solids were filtered, washed with ethanol, diethylether, and dried to yield blue solids of N-hydroxyphenylpyruvylidene-alaninatoaquocopper (II) complex. IR $\upsilon_{max}$ (KBr) 3423, 3255, 2975, 2941, 1621 (s), 1518, 1457, 1396, 1363, 1250, 1154, 1122, 859, 848, 792, 778, 715, 678, and 576.

To a solution of C$_{60}$ (500 mg, 0.69 mmol) in o-dichlorobenzene (150 ml), N-pyruvylidenetyrosinatoaquocopper (II) complex (1.04 g, 3.44 mmol, 5.0 equiv.) or N-hydroxyphenylpyruvylidene-alaninatoaquocopper (II) complex (1.35 g, 4.2 mmol, 6.0 equiv.) in pyridine (40 ml) and triethylamine was added via syringe in sequence under N$_2$. The solution mixture was stirred for a period of 24 h at ambient temperature. Unreacted copper complex partially suspended in the solution was removed. It was added hexane (100 ml) to effect precipitation of solid products. The solid precipitates were isolated by centrifuge, washed with hexane (50 ml), and dried in vaccuo. It was further washed twice by water, brine, and CH$_3$CN (20 ml each) and dried in vaccuo to afford brown solids of 1-dimethyl-3-hydroxyphenylmethyl-fulleropyrrolidine-1,3-dicarboxylatoaquocopper (II) complex (665 mg).

Brown solids of 1-dimethyl-3-hydroxyphenylmethyl-fulleropyrrolidine-1,3-dicarboxylato-aquocopper (II) complex (0.5 g) were dissolved in a mixture of pyridine (25 ml) and water (25 ml) or o-dichlorobenzeneEtOH. It was stirred in the presence of Dowex acid resin (50WX8, 2.0 g) for a period of 4.0 h. The solid resin was filtered off. The remaining solution was stirred further with fresh Dowex acid resin (50WX8, 1.5 g) for an additional 30 min. At the end of the ion exchanging reaction, Dowex resin was filtered. After solvent evaporation of the filtrate, the resulting dark solids were washed with ethanol and dried in vaccuo to give the product of 1-dimethyl-3-hydroxyphenylmethyl-fulleropyrrolidine-1,3-dicarboxylic acid. IR $\upsilon_{max}$ (KBr) 3430 (br, s), 2933 (w), 2866, 1659 (s), 1620, 1517, 1442, 1364, 1321, 1237, 1175, 1112, 821, and 528. Treatment of 1-dimethyl-3-hydroxyphenylmethyl-fulleropyrrolidine-1,3-dicarboxylic acid with dil. HCl (2.0 N) gave the corresponding N-protonated 1,3-dimethyl-fulleropyrrolidine-1,3-dicarboxylic acid containing free carboxylic acids. IR $\upsilon_{max}$ (KBr) 3401 (br, s), 3230, 2933, 2851, 28002500 (br, CO$_2$H), 1758, 1718, 1646 (s), 1516, 1442, 1363, 1320, 1174, 1036, 991, 822, and 504.

EXAMPLE 3

Synthesis of E-isomer of 1-dimethyl-3-(3,4-dihydroxyphenyl)methyl-fulleropyrrolidine-1,3-dicarboxylic acid. In a conical flask charged with 3-(3,4-dihydroxyphenyl)-L-alanine (L-DOPA, 1.0 g, 5.1 mmol) and a mixture of water and ethanol (10 ml, 2:1) and stirred for a period of 20 min was added pyruvic acid (446 mg, 5.1 mmol). The reaction mixture was stirred at 40° C. for 2.0 h. The resulting yellowish solution was then added copper (II) acetate (1.0 g, 5.1 mmol) in water-ethanol (10 ml) and stirred for an additional 24 h, causing precipitation of pale blue solids. The solids were filtered, washed with water, ethanol, and dried to yield N-pyruvylidene-3-(3,4-dihydroxyphenyl)alaninatoaquocopper (II) complex (1.02 g). IR $\upsilon_{max}$ (KBr) 3412 (br, s), 3251 (br, s), 1615 (s), 1500, 1382, 1282, 1251, 1157, 869, 721, and 645.

To a solution of C$_{60}$ (100 mg, 0.14 mmol) in o-dichlorobenzene (40 ml), N-pyruvylidene-3-(3,4-dihydroxyphenyl)alaninatoaquocopper (II) complex (288 mg, 0.84 mmol, 6.0 equiv.) in pyridine (35 ml) was added via syringe under N$_2$. The solution mixture was stirred for a period of 15 h at 50–60° C. It was added hexane (100 ml) to effect precipitation of solid products. The solid precipitates were isolated by centrifuge, washed with hexane (50 ml), and dried in vaccuo. It was further washed twice by water, brine, and CH$_3$CN (20 ml each) and dried in vaccuo to afford dark brown solids of 1-dimethyl-3-(3,4-dihydroxyphenyl)methyl-fulleropyrrolidine-1,3-dicarboxylato-aquocopper (II) complex (150 mg).

Brown solids of 1-dimethyl-3-(3,4-dihydroxyphenyl)methyl-fulleropyrrolidine-1,3-dicarboxyl-atoaquocopper (II) complex (150 mg) were dissolved in a mixture of pyridine (20 ml) and water (20 ml). It was stirred in the presence of Dowex acid resin (50WX8, 1.0 g) for a period of 2.0 h. The solid resin was filtered off. The remaining solution was stirred further with fresh Dowex acid resin (50WX8, 1.0 g) for an additional 30 min. At the end of the ion exchanging reaction, Dowex resin was filtered. After solvent evaporation of the filtrate, the resulting dark solids were washed with ethanol and dried in vaccuo to give the product of 1-dimethyl-3-(3,4-dihydroxyphenyl)methyl-fulleropyrrolidine-1,3-dicarboxylic acid (200 mg). IR $\upsilon_{max}$ (Ker) 3395 (br, s), 2950 (w), 2922 (w), 2800–2500 (br), 1613, 1545, 1470, 1427, 1302, 1187, 1162, 1067 (w), 862, 701 (w), 625 (w), and 525.

EXAMPLE 4

Synthesis of E-isomer of fulleropyrrolidine-1,3-di(3-propanoic acid)-1,3-dicarboxylic acid. In a conical flask charged with L-glutamic acid (1.47 g, 10.0 mmol) and a mixture of water and ethanol (20 ml, 2:1) and stirred for a period of 20 min was added 2-ketoglutaric acid (1.46 g, 10.0 mmol). The reaction mixture was stirred at ambient temperature for a period of 2.0 h at pH 6.07.0 using NaOH as a titrating agent. The resulting colorless solution was then added copper (II) acetate (1.99 g, 10.0 mmol) in water-ethanol (10 ml) and stirred for an additional 2 h, causing precipitation of pale blue solids. The solids were filtered, washed with ethanol and ether, and dried in vaccuo to yield N-(2-ketoglutarylidene)-L-glutamitoaquocopper (II) complex (2.6 g). IR $\upsilon_{max}$ (KBr) 3439 (br, s), 3282 (br, s), 2949, 2581, 1623 (s), 1392, 1343, 1231, 1147, 1095, 939, 676, and 641.

To a solution of $C_{60}$ (400 mg, 0.64 mmol) in o-dichlorobenzene (100 ml), N-(2-ketoglutarylidene)-L-glutamitoaquocopper (II) complex (1.3 g, 6.0 equiv.) in pyridine (50 ml) was added via syringe under $N_2$. The solution mixture was stirred in the presence of 1,8-diazabicyclo[5.4.0]undec-7-ene (DBU, 300 mg) for a period of 5 h at ambient temperature. At the end of reaction, hexane (100 ml) was added to the reaction mixture causing precipitation of solid products. The solid precipitates were isolated by centrifuge, washed with hexane (50 ml), and dried in vaccuo. It was further washed twice by water, brine, and $CH_3CN$ (20 ml each) and dried in vaccuo to afford dark brown solids of fulleropyrrolidine-1,3-di(3-propanoic acid)-1,3-dicarboxylato-aquocopper (II) complex. It was then dissolved in DMSO (30 ml) and treated with Dowex acid resin (50WX8, 1.0 g) for a period of 2.0 h. The solid resin was filtered off. The remaining solution was stirred further with fresh Dowex acid resin (50WX8, 1.0 g) for an additional 30 min. At the end of the ion exchanging reaction, Dowex resin was filtered. Solid products were precipitated from the filtrate by addition of a mixture of ether and acetone. The precipitates were washed with ether and acetone and dried in vaccuo to give brown solids of fulleropyrrolidine-1,3-di(3-propanoic acid)-1,3-dicarboxylic acid (550 mg). IR $\upsilon_{max}$ (KBr) 3422 (br, s), 2928 (w), 2857 (w), 1716, 1635 (s), 1435, 1371, 1200 (w), 1018, 952, and 527. Treatment of fulleropyrrolidine-1,3-di(3-propanoic acid)-1,3-dicarboxylic acid with dil. HCl (2.0 N) gave the corresponding N-protonated fulleropyrrolidine-1,3-di(3-propanoic acid)-1,3-dicarboxylic acid containing free carboxylic acids. IR $\upsilon_{max}$ (KBr) 3433 (br, s), 2928, 2853, 2800-2500 (br, $CO_2H$), 1792 (w), 1721 (s), 1630 (s), 1440, 1411, 1328, 1184, 1004, 949, 764, and 526.

EXAMPLE 5

Synthesis of E-isomer of 1-methyl-3-thiomethyl-fulleropyrrolidine-1,3-dicarboxylic acid. In a conical flask charged with L-cysteine (1.21 g, 10.0 mmol) and a mixture of water and ethanol (20 ml, 2:1) and stirred for a period of 20 min was added pyruvic acid (880 mg, 10.0 mmol). The reaction mixture was stirred at ambient temperature for a period of 1.0 h. The resulting colorless solution was then added copper (II) acetate (1.99 g, 10.0 mmol) in water-ethanol (10 ml) and stirred for an additional 2 h, causing precipitation of dark gray solids. The solids were filtered, washed with ethanol and ether, and dried in vaccuo to yield N-pyruvylidene-L-cysteinatoaquocopper (II) complex (1.6 g). IR $\upsilon_{max}$ (KBr) 3447 (br), 3221 (br), 2994 (w), 2935 (w), 1666, 1625, 1598 (s), 1574 (s), 1423, 1404, 1378, 1315, 1178, 1016, 970, 937, 884, 759, 713, and 642.

To a solution of $C_{60}$ (400 mg, 0.64 mmol) in o-dichlorobenzene (100 ml), N-pyruvylidene-L-cysteinatoaquocopper (II) complex (600 mg, 6.0 equiv.) in pyridine (30 ml) was added via syringe under $N_2$. The mixture was stirred for a short period of 10 min at ambient temperature to give a solution containing suspended brown solids. At the end of reaction, hexane (100 ml) was added to effect complete precipitation of solid products. The solid precipitates were isolated by centrifuge, washed with hexane (50 ml), and dried in vaccuo. It was then dissolved in a mixture of o-dichlorobenzene and ethanol (1:1, 40 ml) and treated with Dowex acid resin (50WX8, 1.0 g) for a period of 2.0 h. The solid resin was filtered off. The remaining solution was stirred further with fresh Dowex acid resin (50WX8, 1.0 g) for an additional 30 min. At the end of the ion exchanging reaction, Dowex resin was filtered. Ethanol was removed from the filtrate and solid products were precipitated by addition of ether to the remaining liquid. The precipitates were washed with ether and dried in vaccuo to give brown solids of 1-methyl-3-thiomethyl-fulleropyrrolidine-1,3-dicarboxylic acid (520 mg). IR $\upsilon_{max}$ (KBr) 3429 (br, s), 2979 (w), 2935 (w), 1721, 1631 (s), 1540 (w), 1377, 1232, 1180, 955 (w), 767, and 525.

EXAMPLE 6

Synthesis of E-isomer of 1-methyl-3-hydroxymethyl-fulleropyrrolidine-1,3-dicarboxylic acid. In a conical flask charged with L-serine (1.19 g, 10.0 mmol) and a mixture of water and ethanol (20 ml, 2:1) and stirred for a period of 20 min was added pyruvic acid (880 mg, 10.0 mmol). The reaction mixture was stirred at ambient temperature for a period of 2.0 h. The resulting colorless solution was then added copper (II) acetate (1.99 g, 10.0 mmol) in water-ethanol (10 ml) and stirred for an additional 2 h, causing precipitation of pale blue solids. The solids were filtered, washed with ethanol and ether, and dried in vaccuo to yield N-pyruvylidene-L-serinatoaquocopper (II) complex (1.7 g). IR $\square_{max}$ (KBr) 3369 (br, s), 2988 (w), 1731, 1625 (s), 1398, 1341, 1222, 1199, 1145 (w), 1106, 1073, 957 (w), 894, 857, 723, 648, and 589.

To a solution of $C_{60}$ (400 mg, 0.64 mmol) in o-dichlorobenzene (100 ml), N-pyruvylidene-L-serinatoaquocopper (II) complex (590 mg, 6.0 equiv.) in pyridine (30 ml) was added via syringe under $N_2$. The mixture was stirred in the presence of triethylamine for a period of 12 h at ambient temperature to give a solution containing suspended brown solids. At the end of reaction, hexane (100 ml) was added to effect complete precipitation of solid products. The solid precipitates were isolated by centrifuge, washed with hexane (50 ml), and dried in vaccuo. It was then dissolved in a mixture of o-dichlorobenzene and ethanol (1:1, 40 ml) and treated with Dowex acid resin (50WX8, 1.0 g) for a period of 2.0 h. The solid resin was filtered off. The remaining solution was stirred further with fresh Dowex acid resin (50WX8, 1.0 g) for an additional 30 min. At the end of the ion exchanging reaction, Dowex resin was filtered. Ethanol was removed from the filtrate and solid products were precipitated by addition of ether to the remaining liquid. The precipitates were washed with ether and dried in vaccuo to give brown solids of 1-methyl-3-hydroxymethyl-fulleropyrrolidine-1,3-dicarboxylic acid (500 mg). IR $\upsilon_{max}$ (KBr) 3445 (br, s), 2926 (w), 2853 (w), 1786, 1729, 1633 (s), 1454 (w), 1381, 1168, 1107, 1076, 1042, and 533. Treatment of 1-methyl-3-hydroxymethyl-fulleropyrrolidine-1,3-dicarboxylic acid with dil. HCl (2.0 N) gave the corresponding N-protonated 1-methyl-3-hydroxymethyl-fulleropyrrolidine-1,3-dicarboxylic acid containing free carboxylic acids. IR $\upsilon_{max}$ (KBr) 3421 (br, s), 3211, 2954, 2800-2500 (br, $CO_2H$), 1762, 1719 ($CO_2H$), 1630 (s), 1428 (w), 1380, 1183, 1112 (w), 1036, 991, 928 (w), 755 (w), 625 (w), and 526.

EXAMPLE 7

Synthesis of E-isomer of 1-isobutyl-3-(o-hydroxyphenyl)-fulleropyrrolidine-1-carboxylic acid. In a conical flask charged with L-leucine (2.44 g, 20.0 mmol) and a mixture of water and ethanol (20 ml, 2:1) and stirred for a period of 20 min was added salicylaldehyde (2.62 g, 20.0 mmol). The reaction mixture was stirred at 50° C. for a period of 5.0 h at pH 7.0 using NaOH as a titrating agent. The resulting pale yellow solution was then added copper (II) acetate (4.0 g, 20.0 mmol) in water-ethanol (10 ml) and stirred for an additional 30 min, causing precipitation of pale blue-green solids. The solids were filtered, washed with ethanol and ether, and dried in vaccuo to yield N-(2-hydroxybenzylidene)-L-leucinatoaquocopper (II) complex (4.5 g). IR $\upsilon_{max}$ (KBr) 3383 (br, w), 3322 (br, w), 3252 (br, w), 2961, 2912, 2875, 1649 (s), 1628, 1606, 1528, 1451, 1336, 1198, 1147, 1079 (w), 861 (w), 802, 767, 730, and 564.

To a solution of $C_{60}$ (1.0 g, 1.3 mmol) in o-dichlorobenzene (300 ml), N-(2-hydroxybenzylidene)-L-leucinatoaquocopper (II) complex (1.64 g, 5.2 mmol, 4.0 equiv.) in pyridine (100 ml) was added via syringe under $N_2$. The mixture was stirred in the presence of 1,8-diazabicyclo [5.4.0]undec-7-ene (DBU, 1.0 g) for a period of 15 h at ambient temperature to give a solution containing suspended brown solids. At the end of reaction, hexane (100 ml) was added to effect complete precipitation of solid products. The solid precipitates were isolated by centrifuge, washed with hexane (50 ml), and dried in vaccuo, yielding 1.4 g of products. It was then dissolved in a mixture of toluene and ethanol (9:1, 100 ml, brown solution) and treated with Dowex acid resin (50WX8, 2.0 g) for a period of 2.04.0 h. The solid resin was filtered off. The remaining solution was stirred further with fresh Dowex acid resin (50WX8, 1.5 g) for an additional 30 min. At the end of the ion exchanging reaction, Dowex resin was filtered. Solvent was removed from the filtrate and resulting solid products were washed with hexane and dried in vaccuo to give brown solids of 1-isobutyl-3-(o-hydroxyphenyl)-fulleropyrrolidine-1-carboxylic acid (900 mg). $R_f$ 0.35 (thin layer chromatography, $SiO_2$, toluene-ethanol/9:1); IR $\upsilon_{max}$ (KBr) 3440 (br, s), 2957, 2929, 2866, 1706, 1619, 1575, 1495 (w), 1446, 1387 (w), 1293 (w), 1252, 1228, 1179, 1155, 1043, and 650; m/z 955 (M+).

EXAMPLE 8

Synthesis of E-isomer of 1-methyl-3-ethyl-3'-(o-hydroxyphenyl)-fulleropyrrolidine-1-carboxylic acid. Into a conical flask charged with L-alanine (1.78 g, 20.0 mmol), molecular sieves (4 Å), and ethanol (20 ml) was added 2-hydroxypropiophenone (3.0 g, 20.0 mmol). The reaction mixture was stirred at the reflux temperature for a period of 24.0 h at pH 8.0 using NaOH as a titrating agent. The resulting yellow solution was then added copper (II) acetate (4.0 g, 20.0 mmol) in water-ethanol (15 ml, 2:1) and stirred for an additional 2.0 h, causing precipitation of green solids. The solids were filtered, washed with ethanol and ether, and dried in vaccuo to yield N-(2-hydroxypropiophenonylidene)-L-alainatoaquocopper (II) complex (4.0 g). IR $\upsilon_{max}$ (KBr) 3470 (br, w), 3305, 3245, 2981, 2933, 2880, 1622 (s), 1575, 1465, 1401, 1363, 1298, 1142, 1125, 1076, 1028, 928, 857, 788, 709, 672, 618, and 575.

To a solution of $C_{60}$ (300 mg, 0.4 mmol) in o-dichlorobenzene (100 ml), N-(2-hydroxypropiophenonylidene)-L-alainatoaquocopper (II) complex (590 mg, 1.8 mmol, 4.5 equiv.) in pyridine (30 ml) was added via syringe under $N_2$. The mixture was stirred in the presence of triethylamine (0.5 ml) for a period of 24 h at ambient temperature to give a solution containing suspended brown solids. At the end of reaction, hexane (50 ml) was added to effect complete precipitation of solid products. The solid precipitates were isolated by centrifuge, washed with hexane (30 ml), and dried in vaccuo. It was then dissolved in a mixture of o-dichlorobenzene and ethanol (1:1, 40 ml) and treated with Dowex acid resin (50WX8, 1.0 g) for a period of 2.0 h. The solid resin was filtered off. The remaining solution was stirred further with fresh Dowex acid resin (50WX8, 1.0 g) for an additional 30 min. At the end of the ion exchanging reaction, Dowex resin was filtered. Solvent was removed from the filtrate and resulting solid products were washed with hexane$CH_3CN$ and dried in vaccuo to give brown solids of 1-methyl-3-ethyl-3'-(o-hydroxyphenyl)fulleropyrrolidine-1-carboxylic acid (310 mg). IR $\upsilon_{max}$ (KBr) 3435 (br, s), 3089, 2933, 1722 (w), 1625 (s), 1520 (w), 1413, 1364, 1308, 1168, 1118 (s), 1037 (s), 1010 (s), 677, and 528. Treatment of 1-methyl-3-ethyl-3'-(o-hydroxyphenyl)-fulleropyrrolidine-1-carboxylic acid with dil. HCl (2.0 N) gave the corresponding N-protonated derivative containing free carboxylic acids. IR $\upsilon_{max}$ (KBr) 3427 (br, s), 2950, 2800–2500 (br, $CO_2H$), 1726 ($CO_2H$), 1637 (s), 1514, 1418 (w), 1258 (w), 1205, 1119, 1038, and 612.

EXAMPLE 9

Synthesis of E-isomer of 1-methyl-3-(2,3,4-trihydroxyphenyl)-fulleropyrrolidine-1-carboxylic acid. In a conical flask charged with L-alanine (0.98 g, 10.0 mmol) and a mixture of water and ethanol (20 ml, 2:1) and stirred for a period of 10 min was added 2.3.4-trihydroxybenzaldehyde (1.54 g, 10.0 mmol). The reaction mixture was stirred at 40° C. for a period of 2.0 h. The resulting yellow solution was then added copper (II) acetate (2.0 g, 10.0 mmol) in water-ethanol (5.0 ml) and stirred for an additional 30 min, causing precipitation of dark green solids. The solids were filtered, washed with ethanol and ether, and dried in vaccuo to yield N-(2.3.4-trihydroxybenzylidene)-L-alainnatoaquocopper (II) complex (1.95 g). IR $\square_{max}$ (KBr) 3322 (br), 3248 (br), 2919, 2853, 1574 (s), 1484, 1443, 1399, 1320, 1278, 1187 (w), 1098, 1041 (w), 791, 731, 671, and 519.

To a solution of $C_{60}$ (300 mg, 0.4 mmol) in o-dichlorobenzene (100 ml), N-(2.3.4-trihydroxybenzylidene)-L-alainnatoaquocopper (II) complex (630 mg, 2.0 mmol, 5.0 equiv.) in pyridine (30 ml) was added via syringe under $N_2$. The mixture was stirred for a period of 15 h at ambient temperature to give a solution containing suspended brown solids. At the end of reaction, hexane (50 ml) was added to effect complete precipitation of solid products. The solid precipitates were isolated by centrifuge, washed with hexane (30 ml), and dried in vaccuo. It was then dissolved in a mixture of o-dichlorobenzene and ethanol (1:1, 40 ml) and treated with Dowex acid resin (50WX8, 1.0 g) for a period of 2.0 h. The solid resin was filtered off. The remaining solution was stirred further with fresh Dowex acid resin (50WX8, 1.0 g) for an additional 30 min. At the end of the ion exchanging reaction, Dowex resin was filtered. Solvent was removed from the filtrate and solids were precipitated by addition of diethylether. The solid precipitates were washed with hexane and dried in vaccuo to give brown solids of 1-methyl-3-(2,3,4-trihydroxyphenyl)-fulleropyrrolidine-1-carboxylic acid (290 mg). IR $\upsilon_{max}$ (KBr) 3422 (br, s), 2972, 2927, 2846, 1706 (w), 1635 (s), 1447, 1374, 1314, 1162, 1013, 951, and 526. Treatment of 1-methyl-3-(2,3,4-trihydroxyphenyl)-fulleropyrrolidine-1-carboxylic acid with dil. HCl (2.0 N) gave the corresponding N-protonated derivative containing free carboxylic acids. IR $\upsilon_{max}$ (KBr) 3420 (br, s), 3245 (br), 2978 (w), 2932 (w), 2857 (w), 2800–2500 (br, $CO_2H$), 1709 ($CO_2H$), 1636 (s), 1448, 1403, 1178, 1129, 1037, 1011, 952, and 527.

EXAMPLE 10

Synthesis of 1,3-dimethyl-N-(p-bromobenzyl)fulleropyrrolidine-1,3-dicarboxylic anhydride. To a solution of 1,3-dimethyl-fulleropyrrolidine-1,3-dicarboxylic acid (220 mg, 0.25 mmol) in a mixture of o-dichlorobenzene and DMSO (6:1, 50 ml), phosphorous pentaoxide (250 mg) was added under $N_2$. The mixture was stirred at 50° C. for a period of 12.0 h to effect dehydrative anhydride formation. At the end of reaction, the insoluble solids were separated by centrifuge. The remaining solution was transferred via syringe into the second reaction flask containing p-bromobenzyl chloride (66 mg, 0.3 mmol) and triethylamine (0.1 ml). The mixture was stirred at 50° C. for an additional 8.0 h under $N_2$. Diethyl ether (50 ml) was then added to effect complete precipitation of solid products. The solid precipitates were isolated by centrifuge, washed with diethyl ether (30 ml), water, ethanol, and diethyl ether in sequence and dried in vacuo to give brown solids of 1,3-dimethyl-N-(p-bromobenzyl)fulleropyrrolidine-1,3-dicarboxylic anhydride (180 mg). $^1$H NMR (two amide isomers in an equal amount) δ 1.14 (s, 6H), 1.24 (s, 6H), 7.75 (dd, 4H), 8.15 (dd, 4H); IR $\upsilon_{max}$ (KBr) 3402 (br, s), 2984, 2925, 1787 (w), 1737 (s), 1630, 1591, 1513 (w), 1399, 1255, 1173, 1094, 1071, 1008, 751, and 527.

EXAMPLE 11

Synthesis of oligo[1,3-dimethyl-fulleropyrrolidine-1,3-dicarboxylic N-amide]. To a solution of 1,3-dimethyl-fulleropyrrolidine-1,3-dicarboxylic acid (220 mg, 0.25 mmol) in a mixture of o-dichlorobenzene and DMSO (6:1, 50 ml), phosphorous pentaoxide (250 mg) was added under $N_2$. The mixture was stirred at 50° C. for a period of 12.0 h to effect dehydrative anhydride formation. At the end of reaction, the insoluble solids were separated by centrifuge. The remaining solution was transferred via syringe under $N_2$ into the second reaction flask containing 1,8-diazabicyclo[5.4.0]undec-7-ene (DBU, 1.0 g). The mixture was stirred at 100° C. for an additional 24.0 h under $N_2$ to afford a dark brown-black solution. Diethyl ether (50 ml) was then added to effect complete precipitation of solid products. The solid precipitates were isolated by centrifuge, washed twice with diethyl ether (30 ml), ethanol, and diethyl ether in sequence. It was treated with dil HCl (2 N) in THF, washed with THF, and dried in vaccuo. to give dark brown solids of oligo[1,3-dimethyl-fulleropyrrolidine-1,3-dicarboxylic N-amide] (165 mg). IR $\upsilon_{max}$ (KBr) 3402 (br, s), 2931, 2861, 1712 (w), 1661 (s), 1613, 1442, 1372, 1324, 1156 (s), 1036 (s), 990, 675, and 611.

EXAMPLE 12

Synthesis of 1,3-dimethyl-N-succinamitofulleropyrrolidine-1,3-dicarboxylic acid, $C_{60}[C(CH_3)CO_2H]_2NCO$—$CH_2CH_2CO_2H$. To a solution of 1,3-dimethyl-fulleropyrrolidine-1,3-dicarboxylic acid (440 mg, 0.5 mmol) in a mixture of o-dichlorobenzene and DMSO (6:1, 80 ml), succinic anhydride (100 mg) and 1,8-diazabicyclo[5.4.0]undec-7-ene (DBU, 1.0 g ) were added under $N_2$. The mixture was stirred at 30° C. for a period of 4.0 h. At the end of reaction, the solution was treated with dil. HCl (2.0 N). Diethyl ether (50 ml) was then added to effect complete precipitation of solid products. The solid precipitates were isolated by centrifuge, washed twice with diethyl ether (30 ml), water, and diethyl ether in sequence and dried in vaccuo to give dark brown solids of 1,3-dimethyl-N-succinamitofulleropyrrolidine-1,3-dicarboxylic acid (480 mg). IR $\upsilon_{max}$ (KBr) 3426 (br, s), 2930, 2595 (br, $CO_2H$), 1752 (w), 1718 (s, $CO_2H$), 1626, 1402, 1180, 1086, 1000, 773 (w), 653 (w), and 525 (w).

EXAMPLE 13

Synthesis of tris(hexadecaanilino)-1,3-dimethyl-N-succinamitofulleropyrrolidine-1,3-dicarboxylate, $C_{60}[C(CH_3)CO$—$(NH$—$C_6H_4$—$N=C_6H_4=N$—$C_6H_4$—$NH$—$C_6H_4$—$)_4$-$H]_2NCO$—$CH_2CH_2CO$—$(NH$—$C_6H_4$—$N=C_6H_4=N$—$C_6H_4$—$NH$—$C_6H_4$—$)_4$—H. To a solution of 1,3-dimethyl-N-succinamito-fulleropyrrolidine-1,3-dicarboxylic acid, $C_{60}[C(CH_3)CO_2H]_2NCO$—$CH_2CH_2CO_2H$, (498 mg, 0.5 mmol) in a mixture of o-dichlorobenzene and DMSO (6:1, 100 ml), hexadecaaniline (emeraldine base form, 2.2 g, 1.5 mmol), 1,3-dicyclohexylcarbodiimide (DCC, 340 mg, 1.65 mmol), and 1-hydroxybenzotriazole (BtOH, 223 mg, 1.65 mmol) were added under $N_2$. The mixture was stirred at 40° C. for a period of 24.0 h. At the end of reaction, the solution was added diethyl ether (100 ml) to effect complete precipitation of solid products. The solid precipitates were isolated by centrifuge, treated with aqueous $NH_4OH$, washed twice with water and diethyl ether and dried in vaccuo to give dark blue solids of tris(hexadecaanilino)-1,3-dimethyl-N-succinamitofulleropyrrolidine-1,3-dicarboxylate (2.5 g). IR $\upsilon_{max}$ (KBr) 3433 (br, s), 3284, 2932 (w), 2859 (w), 1596, 1506 (s), 1305, 1252, 1150, 822, 749, 696, and 506.

EXAMPLE 14

Synthesis of tris(glycylglycyl)-1,3-dimethyl-N-succinamitofulleropyrrolidine-1,3-dicarboxylate, $C_{60}[C(CH_3)CO$—$(NHCH_2CO$—$NHCH_2CO_2H]_2NCO$—$CH_2CH_2CO$—$NHCH_2CO$—$NHCH_2CO_2H$. To a solution of 1,3-dimethyl-N-succinamito-fulleropyrrolidine-1,3-dicarboxylic acid, $C_{60}[C(CH_3)CO_2H]_2NCO$—$CH_2CH_2CO_2H$, (498 mg, 0.5 mmol) in a mixture of o-dichlorobenzene and DMSO (6:1, 100 ml), glycylglycine (198 mg, 1.5 mmol), 1,3-dicyclohexylcarbodiimide (DCC, 340 mg, 1.65 mmol), and 1-hydroxybenzotriazole (BtOH, 223 mg, 1.65 mmol) were added under $N_2$. The mixture was stirred at 40° C. for a period of 24.0 h. At the end of reaction, the solution was added diethyl ether (100 ml) to effect complete precipitation of solid products. The solid precipitates were isolated by centrifuge, treated with dil. HCl (2.0 N), washed twice with water and diethyl ether and dried in vaccuo. to give dark brown solids of tris(glycylglycyl)-1,3-dimethyl-N-succinamitofulleropyrrolidine-1,3-dicarboxylate (480 mg). IR $\upsilon_{max}$ (KBr) 3431 (br, s), 2929, 2860 (w), 1773, 1701, 1654 (s), 1550, 1391, 1227, 1178, 1056 (w), 999 (w), and 527.

EXAMPLE 15

Detection of high free radical scavenging potency of hydrophilic fullerene derivatives. The xanthine/xanthine oxidase enzymatic system is highly effective for the production of superoxide radicals ($O_2^-$). Reaction of superoxide radicals with cytochrome ($Fe^{+3}$) C may result in a product of reduced cytochrome ($Fe^{+2}$) C which shows a respectable optical absorption at 550 nm. Therefore, the detected optical absorption intensity of the reduced cytochrome ($Fe^{+2}$) C can be correlated to the quantity of superoxide radicals reacted with cytochrome ($Fe^{+3}$) C. Scavenging of superoxide radicals by hydrophilic fullerene derivatives in the bio-medium inhibits the formation of reduced cytochrome (Fe+2) C and thus reduce the optical absorption at 550 nm.

In one experiment, xanthine (50 μM) was added to a physiological medium (3 ml) containing cytochrome C (10 μM), ethylenediaminetetraacetic acid (EDTA) (10 mM) and a phosphate buffer (50 mM) at pH 7.8. The mixture was then added xanthine oxidase in quantity enough to induce 0.025 unit of optical absorption at 550 nm per 5 min (Mc Cord, et al. *J. Biol. Chem.* 1969, 244, 6049.). Subsequently, 1,3-dimethyl-N-succinamitofulleropyrrolidine-1,3-dicarboxylic acid, $C_{60}[C(CH_3)CO_2H]_2NCO$—$CH_2CH_2CO_2H$, prepared in Example 12, in a concentration of 0, 5.0, 10.0, 25.0, 50, and 100 μM was added in separated runs while the absorption intensity of the reduced cytochrome C was recorded. A rapid decrease of reduced cytochrome C to roughly 50% and 20% of the control value was obtained with the dose of 1,3-dimethyl-N-succinamitofulleropyrrolidine-1,3- dicarboxylic acid as 25 and 100 μM, respectively. These results substantiated efficient scavenging of superoxide radicals by 1,3-dimethyl-N-succinamitofulleropyrrolidine-1,3-dicarboxylic acid that led to the inhibition of cytochrome C reduction.

EXAMPLE 16

The growth inhibitory effect of 1,3-dimethyl-N-succinamitofulleropyrrolidine-1,3-dicarboxylic acid, $C_{60}[C(CH_3)CO_2H]_2NCO-CH_2CH_2CO_2H$, which was prepared as described in Example 12, on fibrosarcoma tumor cells upon photo-irradiation was studied in vitro. Fibrosarcoma tumor cells (0.5 ml, 4×10$^4$/ml, CCRC 60037) were grown in the MEM medium in a 24-well plate for a period of 24 h. It was treated by 1,3-dimethyl-N-succinamitofulleropyrrolidine-1,3-dicarboxylic acid in a concentration of 0.0, 2.5, 5.0, 7.5, and 10.0 μM for a period of 24 hours. The MEM medium was removed and replaced by the fresh medium (1.0 ml). The cell-containing plates were exposed to a fluorescence light source (27 W) in a distance of 5–6 cm for a period of 10, 20, 40, and 60 min. The plates were then kept in incubator at 37° C. a period of 48 h. Measurement of cell viability in each plate was performed by the MTT assay using optical absorption at 540 nm. The data indicated a rapid decrease in the tumor cell count under application of 1,3-dimethyl-N-succinamitofulleropyrrolidine-1,3-dicarboxylic acid in a concentration of only 2.5 μM with a photo-irradiation period of more than 20 min. These results substantiated high efficacy of the growth inhibition on fibrosarcoma tumor cells upon photo-irradiation.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:
1. A compound of formula (I):

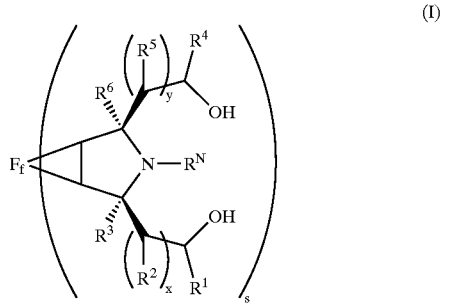

(I)

wherein
$F_f$ is $F(-K)_m(-Y-Z)_q$ in which F is a fullerene core; each K, independently, is $-OH$, $-SH$, $-NH_2$, $-NHOH$, $-SO_3H$, $-OSO_3H$, $-CO_2H$, $-CONH_2$, $-CONHNH_2$, $-P(OH)_3$, $-PO(OH)_2$, $-O-PO(OH)_2$, $-O-PO(OH)-O-PO(OH)_2$, $-O-PO(O^-)-O-CH_2CH_2-NH_3^+$, $-O-PO(O^-)-O-CH_2CH_2-N^+(CH_3)_3$, -glycoside, $-OCH_3$, $-OCH_2(CHOH)_4-CH_2OH$, $-OCH_2(CHOH)_2-CH_2OH$, $-NH-CH_2-CO_2H$, $-[CH(CO_2H)-CH_2]_{1-100}-OH$, $-[CH(CO_2R^a)-CH_2]_{1-100}-OH$, $-[C(CH_3)(CO_2H)-CH_2]_{1-100}-OH$, $-[C(CH_3)(CO_2 R^a)-CH_2]_{1-100}-OH$, $-N(OH)_2$, $-NH_3^+$, $-N^+H_2R^a$, $-N^+HR^aR^b$, or $-N^+R^aR^bR^c$; each Y is $-A-B-$, in which A is $-O-$, $-NH-$, $-S-$, $-CO-O-$, $-O-CO-$, $-O-CO-O-$, $-O-CO-NH-$, $-NH-CO-NH-$, $-CO-NH-$, or $-NH-CO-$; and B is $-R^a-O-[Si(CH_3)_2-O-]_{1-100}$, $C_{1-2000}$ alkyl, $C_{6-40}$ aryl, $C_{7-2000}$ alkylaryl, $C_{7-2000}$ arylalkyl, $(C_{1-30}$ alkyl ether$)_{1-100}$, $(C_{6-40}$ aryl ether$)_{1-100}$, $(C_{7-2000}$ alkylaryl ether$)_{1-100}$, $(C_{7-2000}$ arylalkyl ether$)_{1-100}$, $(C_{1-30}$ alkyl thioether$)_{1-100}$, $(C_{6-40}$ aryl thioether$)_{1-100}$, $(C_{7-2000}$ alkylaryl thioether$)_{1-100}$, $(C_{7-2000}$ arylalkyl thioether$)_{1-100}$, $(C_{2-50}$ alkyl ester$)_{1-100}$, $(C_{7-2000}$ aryl ester$)_{1-100}$, $(C_{8-2000}$ alkylaryl ester$)_{1-100}$, $(C_{8-2000}$ arylalkyl ester$)_{1-100}$, $-R^a-CO-O-(C_{1-30}$ alkyl ether$)$, $-R^a-CO-O-(C_{6-40}$ aryl ether$)_{1-100}$, $-R^a-CO-O-(C_{7-2000}$ alkylaryl ether$)_{1-100}$, $R^a-CO\_O-(C_{7-2000}$ arylalkyl ether$)_{1-100}$, $(C_{4-50}$ alkyl urethane$)_{1-100}$, $(C_{14-60}$ aryl urethane$)_{1-100}$, $(C_{10-2000}$ alkylaryl urethane$)_{1-100}$, $(C_{10-2000}$ arylalkyl urethane$)_{1-100}$, $(C_{5-50}$ alkyl urea$)_{1-100}$, $(C_{14-60}$ aryl urea$)_{1-100}$, $(C_{10-2000}$ alkylaryl urea$)_{1-100}$, $(C_{10-2000}$ arylalkyl urea$)_{1-100}$, $(C_{2-50}$ alkyl amide$)_{1-100}$, $(C_{7-60}$ aryl amide$)_{1-100}$, $(C_{8-2000}$ alkylaryl amide$)_{1-100}$, $(C_{8-2000}$ arylalkyl amide$)_{1-100}$, $(C_{3-30}$ alkyl anhydride$)_{1-100}$, $(C_{8-50}$ aryl anhydride$)_{1-100}$, $(C_{9-2000}$ alkylaryl anhydride$)_{1-100}$, $(C_{9-2000}$ arylalkyl anhydride$)_{1-100}$, $(C_{2-30}$ alkyl carbonate$)_{1-100}$, $(C_{7-50}$ aryl carbonate$)_{1-100}$, $(C_{8-2000}$ alkylaryl carbonate$)_{1-100}$, $(C_{8-2000}$ arylalkyl carbonate$)_{1-100}$, $-R^a-O-CO-NH-(R^b$ or $Ar-R^b-Ar)-NH-CO-O-(C_{1-30}$alkyl ether, $C_{6-40}$ aryl ether, $C_{7-2000}$ alkylaryl ether, or $C_{7-2000}$ arylalkyl ether$)_{1-100}$, $-R^a-O-CO-NH-(R^b$ or $Ar-R^b-Ar)-NH-CO-O-(C_{2-50}$ alkyl ester, $C_{7-60}$ aryl ester, $C_{8-2000}$ alkylaryl ester, or $C_{8-2000}$ arylalkyl ester$)_{1-100}$, $-R^a-O-CO-NH-(R^b$ or $Ar-R^b-Ar)-NH-CO-O-(C_{1-30}$ alkyl ether, $C_{6-40}$ aryl ether, $C_{7-2000}$ alkylaryl ether, or $C_{7-2000}$ arylalkyl ether$)_{1-100}-CO-NH-(R^b$ or $Ar-R^b-Ar)-NH-CO-O-$, $-R^a-O-CO-NH-(R^b$ or $Ar-R^b-Ar)-NH-CO-O-(C_{2-50}$ alkyl ester, $C_{7-60}$ aryl ester, $C_{8-2000}$ alkylaryl ester, or $C_{8-2000}$ arylalkyl ester$)_{1-100}-R^c-O-CO-NH-(R^b$ or $Ar-R^b-Ar)-NH-CO-O-$, $-R^a-NH-CO-NH-(R^b$ or $Ar-R^b-Ar)-NH-CO-O-(C_{1-30}$ alkyl ether, $C_{6-40}$ aryl ether, $C_{7-2000}$ alkylaryl ether, or $C_{7-2000}$ arylalkyl ether$)_{1-100}$, $-R^a-NH-CO-NH-(R^b$ or $Ar-R^b-Ar)-NH-CO-O-(C_{2-50}$ alkyl ester, $C_{7-60}$ aryl ester, $C_{8-2000}$ alkylaryl ester, or $C_{8-2000}$ arylalkyl ester$)_{1-100}$, $-R^a-NH-CO-NH-(R^b$ or $Ar-R^b-Ar)-NH-CO-O-(C_{1-30}$ alkyl ether, $C_{6-40}$ aryl ether, $C_{7-2000}$ alkylaryl ether, or $C_{7-2000}$ arylalkyl ether$)_{1-100}-CO-NH-(R^b$ or $Ar-R^b-Ar)-NH-CO-O-$, $-R^a-NH-CO-NH-(R^b$ or $Ar-R^b-Ar)-NH-CO-O-(C_{2-50}$ alkyl ester, $C_{7-60}$ aryl ester, $C_{8-2000}$ alkylaryl ester, or $C_{8-2000}$ arylalkyl ester$)_{1-100}-R^c-O-CO-NH-(R^b$ or $Ar-R^b-Ar)-NH-CO-O-$, $-R^a-O-CO-NH-(R^b$ or $Ar-R^b-Ar)-NH-CO-NH-(C_{2-50}$ alkyl amide, $C_{7-60}$ aryl amide, $C_{8-2000}$ alkylaryl amide, or $C_{8-2000}$ arylalkyl amide$)_{1-100}$, $-R^a-NH-CO-NH-(R^b$ or $Ar-R^b-Ar)-NH-CO-NH-(C_{2-50}$ alkyl amide, $C_{7-60}$ aryl amide, $C_{8-2000}$ alkylaryl amide, or $C_{8-2000}$ arylalkyl amide$)_{1-100}$, or a bond; each Z, independently, is $-G-D$, wherein G is $-R^a-$, $-R^a-Ar-$, $-Ar-R^a-$, or $-Ar-$; and D is $-H$, $-OH$, $-SH$, $-NH_2$, $-NHOH$, $-SO_3H$, $-OSO_3H$, $-CO_2H$, $-CONH_2$, —CONHNH$_2$, —CH(NH$_2$)—CO$_2$H, —NH—CH$_2$—CO$_2$H, —P(OH)$_3$, —PO(OH)$_2$, —O—PO(OH)$_2$, —O—PO(OH)—O—PO(OH)$_2$, —O—PO(O$^-$)—O—CH$_2$CH$_2$NH$_3$$^+$, —O—PO(O$^-$)—O—CH$_2$CH$_2$—N$^+$(CH$_3$)$_3$, -glycoside, -oligosaccharide, —CO-glycoside, —CO-oligosaccharide, —OCH$_3$, —OCH$_2$(CHOH)$_4$—CH$_2$OH, —OCH$_2$(CHOH)$_2$—CH$_2$OH, —CO—OCH$_2$(CHOH)$_4$—CH$_2$OH, —C$_6$H$_3$(OH)$_2$, —N(CH$_2$CO$_2$H)$_2$, —CO—N(CH$_2$CO$_2$H)$_2$, —CO—NH—C(CH$_2$CH$_2$CO$_2$H)$_3$, —CO—NH—C(CH$_2$CH$_2$OH)$_3$, —[CH$_2$—CH(CO$_2$R$^a$)]$_{1-100}$—H, —NH$_3$$^+$, —N$^+$H$_2$R$^a$, —N$^+$HR$^a$R$^b$, or —N$^+$R$^a$R$^b$R$^c$, each of R$^a$, R$^b$, and R$^c$, independently, being C$_{1-20}$ alkyl and Ar being aryl; q is 0–30; and m is 0–30; provided that the sum of q and m is 0–30;

each of R$^1$ and R$^4$, independently, is =O or C$_{1-20}$ hydrocarbon; and each of R$^2$ and R$^5$, independently, is C$_{1-20}$ hydrocarbon; wherein R$^1$ and R$^2$, or R$^4$ and R$^5$ can join together to form C$_{6-40}$ aryl which is optionally substituted with halide, —OH, —NHNH$_2$, —NH$_2$OH, —NH—CH$_2$—CO$_2$H, —CH$_2$—CH$_2$—D, —CH$_2$—B—Z, —CO—CH$_2$—D, —CO—B—Z, —O—B—Z, or —NH—B—Z; each of B, D, and Z having been defined above;

each of R$^3$ and R$^6$, independently, is —H, —CH$_2$—D, —B—Z, —G—E, —G—CO—E, or a side chain of an amino acid; each of B, D, and Z having been defined above, and E being E$_1$, E$_2$, or E$_3$, in which E$_1$ is Y$_1$,Y$_2$-amino, (Y$_1$,Y$_2$-alkyl)-amino, Y$_1$,Y$_2$-ethylenediamino, (dihydroxymethyl)alkylamino, (X$_1$,X$_3$-aryl)amino, or X$_1$,X$_3$-aryloxy; E$_2$ is Y$_1$,Y$_2$-alkoxy, (Y$_1$,Y$_2$-amino)alkoxy, (Y$_1$,Y$_2$,Y$_3$-aryl)oxy, (dihydroxyalkyl)-aryloxy, (Y$_1$,Y$_2$,Y$_3$-alkyl)amino, (Y$_1$,Y$_2$,Y$_3$-aryl)amino, dihydroxyalkylamino, Y$_1$,Y$_2$,Y$_3$-alkoxy, (trihydroxyalkyl)alkoxy, (trihydroxyalkyl)alkylamino, (dicarboxyalkyl)amino, (Y$_1$,Y$_2$,Y$_3$-alkyl)thio, (X$_1$,X$_3$-aryl)thio, (Y$_1$,Y$_2$-alkyl)thio, (dihydroxyalkyl)thio, Y$_1$,Y$_2$-dioxoalkyl, or tri-(Y$_1$,Y$_2$,Y$_3$-methylaminocarboxyethyl)methylamino; and E$_3$ is ((glycosidyl)oxoheteroaryl)amino, ((glycosidyl)oxoaryl)amino, (X$_1$,X$_2$,X$_3$-heteroaryl)amino, (X$_1$-diarylketone)amino, (X,X$_1$-oxoaryl)amino, (X,X$_1$-dioxoaryl)amino, (Y$_1$-alkyl,Y$_2$-alkyldioxoheteroaryl)amino, (Y$_1$-alkyl,Y$_2$-alkyldioxoaryl)amino, (di(Y$_1$,Y$_2$-methyl)dioxoheteroaryl)amino, (di(Y$_1$,Y$_2$-methyl)dioxoaryl)amino, ((glycosidyl)heteroaryl)amino, ((glycosidyl)aryl)amino, ((carboxylacetylalkyl)oxoheteroaryl)amino, ((carboxylacetylalkyl)oxoaryl)amino, ((isopropylaminohydroxy-alkoxy)aryl)amino, (X$_1$,X$_2$,X$_3$-alkylaryl)amino, (X$_1$,X$_2$,X$_3$-heteroaryl)oxy, (isopropylaminohydroxyalkyl)aryloxy, (X$_1$,X$_2$,X$_3$-oxoheteroaryl)oxy, (X$_1$,X$_2$,X$_3$-oxoaryl)oxy, (X$_1$,Y$_1$-oxoheteroaryl)oxy, (X$_1$-diarylketone)oxy, (X,X$_1$-oxoaryl)oxy, (X$_1$,X$_2$-dioxoaryl)oxy, (Y$_1$,Y$_2$,di-aminodihydroxy)alkyl, (X$_1$,X$_2$-heteroaryl)thio, ((tricarboxylalkyl)ethylene-diamino)alkoxy, (X$_1$,X$_2$-oxoaryl)thio, (X$_1$,X$_2$-dioxoaryl)thio, (glycosidylheteroaryl)thio, (glycosidylaryl)thio, Y$_1$-alkyl(thiocarbonyl)thio, Y$_1$,Y$_2$-alkyl(thiocarbonyl)thio, Y$_1$,Y$_2$,Y$_3$-alkyl(thiocarbonyl)thio, (Y$_1$,Y$_2$-aminothiocarbonyl)thio, (pyranosyl)thio, cysteinyl, tyrosinyl, (phenylalainyl)amino, (dicarboxyalkyl)thio, (aminoaryl)$_{1-100}$amino, (pyranosyl)amino, (Y$_1$-aminoaryl)$_{1-100}$amino, (amino(sulfoaryl))$_{1-100}$amino, peptidyl, thymidinyl, uridinyl, guanosinyl, adenosinyl, cholesteryl, or biotinylalkoxy; wherein X is halide; each of X$_1$, X$_2$, and X$_3$, independently is —Y$_1$, —O—Y$_1$, —S—Y$_1$, —NH—Y$_1$, —CO—O—Y$_1$, —O—CO—Y$_1$, —CO—NH—Y$_1$, —CO—NY$_1$Y$_2$, —NH—CO—Y$_1$, —SO$_2$—Y$_1$, —CHY$_1$Y$_2$, or —NY$_1$Y$_2$; and each of Y$_1$, Y$_2$, and Y$_3$, independently, is —Z or —B—Z;

R$^N$ is H; or one of R$^3$ and R$^6$, together with R$^N$ is a bond and the other of R$^3$ and R$^6$ is as defined above.

each of x and y, independently, is 0 or 1; and s is 1–6;

provided that when x is 0, R$^1$ is =O; that when y is 0, R$^4$ is =O; that when x is 1, R$^1$ and R$^2$ join together to form C$_{6-40}$ aryl; and that when y is 1, R$^4$ and R$^5$ join together to form C$_{6-40}$ aryl; and or a salt thereof.

2. The compound of claim 1, wherein at least one of x and y is 1.

3. The compound of claim 2, wherein R$^1$ and R$^2$, or R$^4$ and R$^5$ can join together to form a benzene ring.

4. The compound of claim 3, wherein F is C$_{60}$, C$_{61}$, C$_{62}$, C$_{63}$, C$_{64}$, C$_{65}$, C$_{70}$, C$_{76}$, C$_{78}$, C$_{82}$, C$_{84}$, or C$_{92}$, or La@C$_n$, Ho@C$_n$, Gd@C$_n$, or Er@C$_n$, in which n is 60, 74, or 82.

5. The compound of claim 3, wherein the sum of q and m is 0–20.

6. The compound of claim 3, wherein each K, independently, is —SH, —NHOH, —SO$_3$H, —OSO$_3$H, —CONH$_2$, —CONHNH$_2$, —P(OH)$_3$, —PO(OH)$_2$, —O—PO(OH)$_2$, —O—PO(OH)—O—PO(OH)$_2$, —O—PO(O—)—O—CH$_2$CH$_2$NH$_3$$^+$, -glycoside, —O—CH$_2$—(CHOH)$_4$—CH$_2$OH, —O—CH$_2$—(CHOH)$_2$—CHOH, —N$^+$HR$^a$R$^b$, or N$^+$HR$^a$R$^b$R$^c$.

7. The compound of claim 3, wherein D is —SH, —NHOH, —SO$_3$H, —OSO$_3$H, —CONH$_2$, —CONHNH$_2$, —P(OH)$_3$, —PO(OH)$_2$, —O—PO(OH)$_2$, —O—PO(OH)—O—PO(OH)$_2$, —O—PO(O$^-$)—O—CH$_2$CH$_2$NH$_3$$^+$, -glycoside, -oligosaccharide, —CO-glycoside, —CO-oligosaccharide, —O—CH$_2$—(CHOH)$_4$—CH$_2$OH, —O—CH$_2$—(CHOH)$_2$—CHOH, —N$^+$HR$^a$R$^b$, or N$^+$HR$^a$R$^b$R$^c$.

8. The compound of claim 3, wherein only one of x and y is 1.

9. The compound of claim 8, wherein x is 1, y is 0, and R$^1$ and R$^2$ join together to form a benzene ring.

10. The compound of claim 9, wherein R$^3$ is —H, —B—Z, —G—E, or —G—CO—E.

11. The compound of claim 9, wherein R$^6$ is —G—E, —G—CO—E, or a side chain of an amino acid.

12. The compound of claim 11, wherein R$^6$ is a side chain of alanine, aspartic acid, cysteine, glutamic acid, phenylalanine, halophenylalanine, hydroxyphenylalanine, glycine, histidine, isoleucine, lysine, leucine, methionine, asparagine, glytamine, arginine, serine, theronine, valine, tryptophan, tyrosine, 2-aminobutyric acid, halophenylalanine, cyclohexylalanine, citrulline, homocitrulline, homoserine, norleucine, norvaline, or ornithine.

13. The compound of claim 12, wherein R$^3$ is —H, —B—Z, —G—E, or —G—CO—E.

14. The compound of claim 13, wherein F is C$_{60}$, and the sum of q and m is 0–20.

15. The compound of claim 14, said compound is the E-isomer of 1-dimethyl-3-hydroxyphenylmethyl-fulleropyrrolidine-1,3-dicarboxylic acid, 1-dimethyl-3-(3,4-dihydroxyphenyl)methyl-fulleropyrrolidine-1,3-dicarboxylic acid, 1-isobutyl-3-(o-hydroxyphenyl)-fulleropyrrolidine-1-carboxylic acid, 1-methyl-3-ethyl-3'-(o-hydroxyphenyl)-fulleropyrrolidine-1-carboxylic acid, or 1-methyl-3-(2,3,4-trihydroxyphenyl)-fulleropyrrolidine-1-carboxylic acid.

16. The compound of claim 1, wherein both x and y are 0.

17. The compound of claim 16, wherein F is $C_{60}$, $C_{61}$, $C_{62}$, $C_{63}$, $C_{64}$, $C_{65}$, $C_{70}$, $C_{76}$, $C_{78}$, $C_{82}$, $C_{84}$, or $C_{92}$, or La@$C_n$, Ho@$C_n$, Gd@$C_n$, or Er@$C_n$, in which n is 60, 74, or 82.

18. The compound of claim 16, wherein the sum of q and m is 0–20.

19. The compound of claim 16, wherein each K, independently, is —SH, —NHOH, —$SO_3H$, —$OSO_3H$, —$CONH_2$, —$CONHNH_2$, —$P(OH)_3$, —$PO(OH)_2$, —O—$PO(OH)_2$, —O—PO(OH)—O—$PO(OH)_2$, —O—PO($O^-$)—O—$CH_2CH_2NH_3^+$, -glycoside, —O—$CH_2$—$(CHOH)_4$—$CH_2OH$, —O—$CH_2$—$(CHOH)_2$—CHOH, —$N^+HR^aR^b$, or $N^+HR^aR^bR^c$.

20. The compound of claim 16, wherein D is —SH, —NHOH, —$SO_3H$, —$OSO_3H$, —$CONH_2$, —$CONHNH_2$, —$P(OH)_3$, —$PO(OH)_2$, —O—$PO(OH)_2$, —O—PO(OH)—O—$PO(OH)_2$, —O—PO($O^-$)—O—$CH_2CH_2NH_3^+$, -glycoside, -oligosaccharide, —CO-glycoside, —CO-oligosaccharide, —O—$CH_2$—$(CHOH)_4$—$CH_2OH$, —O—$CH_2$—$(CHOH)_2$—CHOH, —$N^+HR^aR^b$, or $N^+HR^aR^bR^c$.

21. The compound of claim 16, wherein each of $R^3$ and $R^6$, independently, is —B—Z, —G—E, —G—CO—E, or a side chain of alanine, aspartic acid, cysteine, glutamic acid, phenylalanine, halophenylalanine, hydroxyphenylalanine, glycine, histidine, isoleucine, lysine, leucine, methionine, asparagine, glytamine, arginine, serine, theronine, valine, tryptophan, tyrosine, 2-aminobutyric acid, halophenylalanine, cyclohexylalanine, citrulline, homocitrulline, homoserine, norleucine, norvaline, or ornithine.

22. The compound of claim 21, wherein F is $C_{60}$, and the sum of q and m is 0–20.

23. The compound of claim 22, said compound is the E-isomer of 1,3-dimethyl-fulleropyrrolidine-1,3-dicarboxylic acid, fulleropyrrolidine-1,3-di(3-propanoic acid)-1,3-dicarboxylic acid, 1-methyl-3-thiomethyl-fulleropyrrolidine-1,3-dicarboxylic acid, or 1-methyl-3-hydroxymethyl-fulleropyrrolidine-1,3-dicarboxylic acid.

24. A method for preparing a compound of formula (I-A):

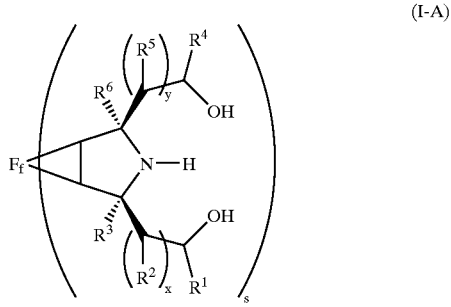

(I-A)

wherein $F_f$ is F(—K)$_m$(—Y—Z)$_q$ in which F is a fullerene core; each K, independently, is —OH, —SH, —$NH_2$, —NHOH, —$SO_3H$, —$OSO_3H$, —$CO_2H$, —$CONH_2$, —$CONHNH_2$, —$P(OH)_3$, —$PO(OH)_2$, —O—$PO(OH)_2$, —O—PO(OH)—O—$PO(OH)_2$, —O—PO($O^-$)—O—$CH_2CH_2$—$NH_3^+$, —O—PO($O^-$)—O—$CH_2CH_2$—$N^+(CH_3)_3$, -glycoside, —$OCH_3$, —$OCH_2(CHOH)_4$—$CH_2OH$, —$OCH_2(CHOH)_2$—$CH_2OH$, —NH—$CH_2$—$CO_2H$, —[CH($CO_2H$)—$CH_2$]$_{1-100}$—OH, —[CH($CO_2R^a$)—$CH_2$]$_{1-100}$—OH, —[C($CH_3$)($CO_2H$)—$CH_2$]$_{1-100}$—OH, —[C($CH_3$)($CO_2$ $R^a$)—$CH_2$]$_{1-100}$—OH, —N(OH)$_2$, —$NH_3^+$, —$N^+H_2R^a$, —$N^+HR^aR^b$, or —$N^+R^aR^bR^c$; each Y is —A—B—, in which A is —O—, —NH—, —S—, —CO—O—, —O—CO—, —O—CO—O—, —O—CO—NH—, —NH—CO—NH—, —CO—NH—, or —NH—CO—; and B is —$R^a$—O—[Si($CH_3$)$_2$—O—]$_{1-100}$, $C_{1-2000}$ alkyl, $C_{6-40}$ aryl, $C_{7-2000}$ alkylaryl, $C_{7-2000}$ arylalkyl, ($C_{1-30}$ alkyl ether)$_{1-100}$, ($C_{6-40}$ aryl ether)$_{1-100}$, ($C_{7-2000}$ alkylaryl ether)$_{1-100}$, ($C_{7-2000}$ arylalkyl ether)$_{1-100}$, ($C_{1-30}$ alkyl thioether)$_{1-100}$, ($C_{6-40}$ aryl thioether)$_{1-100}$, ($C_{7-2000}$ alkylaryl thioether)$_{1-100}$, ($C_{7-2000}$ arylalkyl thioether)$_{1-100}$, ($C_{2-50}$ alkyl ester)$_{1-100}$, ($C_{7-2000}$ aryl ester)$_{1-100}$, ($C_{8-2000}$ alkylaryl ester)$_{1-100}$, ($C_{8-2000}$ arylalkyl ester)$_{1-100}$, —$R^a$—CO—O—($C_{1-30}$ alkyl ether)$_{1-100}$, —$R^a$—CO—O—($C_{6-40}$ aryl ether)$_{1-100}$, —$R^a$—CO—O—($C_{7-2000}$ alkylaryl ether)$_{1-100}$, —$R^a$—CO—O—($C_{7-2000}$ arylalkyl ether)$_{1-100}$, ($C_{4-50}$ alkyl urethane)$_{1-100}$, ($C_{14-60}$ aryl urethane)$_{1-100}$, ($C_{10-2000}$ alkylaryl urethane)$_{1-100}$, ($C_{10-2000}$ arylalkyl urethane)$_{1-100}$, ($C_{5-50}$ alkyl urea)$_{1-100}$, ($C_{14-60}$ aryl urea)$_{1-100}$, ($C_{10-2000}$ alkylaryl urea)$_{1-100}$, ($C_{10-2000}$ arylalkyl urea)$_{1-100}$, ($C_{2-50}$ alkyl amide)$_{1-100}$, ($C_{7-60}$ aryl amide)$_{1-100}$, ($C_{8-2000}$ alkylaryl amide)$_{1-100}$, ($C_{8-2000}$ arylalkyl amide)$_{1-100}$, ($C_{3-30}$ alkyl anhydride)$_{1-100}$, ($C_{8-50}$ aryl anhydride)$_{1-100}$, ($C_{9-2000}$ alkylaryl anhydride)$_{1-100}$, ($C_{9-2000}$ arylalkyl anhydride)$_{1-100}$, ($C_{2-30}$ alkyl carbonate)$_{1-100}$, ($C_{7-50}$ aryl carbonate)$_{1-100}$, ($C_{8-2000}$ alkylaryl carbonate)$_{1-100}$, ($C_{8-2000}$ arylalkyl carbonate)$_{1-100}$, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$—CO—NH—($R^b$ or Ar—$R^b$—Ar)—NH—CO—O—, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$—$R^c$—O—CO—NH—($R^b$ or Ar—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$, —$R^a$—NH_CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$—CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$—$R^c$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$, or a bond; each Z, independently, is —G—D, wherein G is —$R^a$—, —$R^a$—Ar—, —Ar—$R^a$—, or —Ar—; and D is —H, —OH, —SH, —NH$_2$, —NHOH, —SO$_3$H, —OSO$_3$H, —CO$_2$H, —CONH$_2$, —CONHNH$_2$, —CH(NH$_2$)—CO$_2$H, —NH—CH$_2$—CO$_2$H, —P(OH)$_3$, —PO(OH)$_2$, —O—PO(OH)$_2$, —O—PO(OH)—O—PO(OH)$_2$, —O—PO(O$^-$)—O—CH$_2$CH$_2$NH$_3^+$, —O—PO(O$^-$)—O—CH$_2$CH$_2$—N$^+$(CH$_3$)$_3$, -glycoside, -oligosaccharide, —CO-glycoside, —CO-oligosaccharide, —OCH$_3$, —OCH$_2$(CHOH)$_4$—CH$_2$OH, —OCH$_2$(CHOH)$_2$—CH$_2$OH, —CO—OCH$_2$(CHOH)$_4$—CH$_2$OH, —C$_6$H$_3$(OH)$_2$, —N(CH$_2$CO$_2$H)$_2$, —CO—N(CH$_2$CO$_2$H)$_2$, —CO—NH—C(CH$_2$CH$_2$CO$_2$H)$_3$, —CO—NH—C(CH$_2$CH$_2$OH)$_3$, —[CH$_2$—CH(CO$_2$R$^a$)]$_{1-100}$—H, —NH$_3^+$, —N$^+$H$_2$R$^a$, N$^+$HR$^a$R$^b$, or —N$^+$R$^a$R$^b$R$^c$, each of R$^a$, R$^b$, and R$^c$, independently, being C$_{1-20}$ alkyl and Ar being aryl; q is 0–30; and m is 0–30; provided that the sum of q and m is 0–30;

each of R$^1$ and R$^4$, independently, is =O or C$_{1-20}$ hydrocarbon; and each of R$^2$ and R$^5$, independently, is C$_{1-20}$ hydrocarbon; wherein R$^1$ and R$^2$, or R$^4$ and R$^5$ can join together to form C$_{6-40}$ aryl which is optionally substituted with halide, —OH, —NHNH$_2$, —NH$_2$OH, —NH—CH$_2$—CO$_2$H, —CH$_2$—CH$_2$—D, —CH$_2$—B—Z, —CO—CH$_2$—D, —CO—B—Z, —O—B—Z, or —NH—B—Z; each of B, D, and Z having been defined above;

each of R$^3$ and R$^6$, independently, is —H, —CH$_2$—D, —B—Z, —G—E, —G—CO—E or a side chain of an amino acid; each of B, D, and Z having been defined above, and E being E$_1$, E$_2$, or E$_3$, in which E$_1$ is Y$_1$,Y$_2$-amino, (Y$_1$,Y$_2$-alkyl)-amino, Y$_1$,Y$_2$-ethylenediamino, (dihydroxymethyl)alkylamino, (X$_1$,X$_3$-aryl)amino, or X$_1$,X$_3$-aryloxy; E$_2$ is Y$_1$,Y$_2$-alkoxy, (Y$_1$,Y$_2$-amino)alkoxy, (Y$_1$,Y$_2$,Y$_3$-aryl)oxy, (dihydroxyalkyl)-aryloxy, (Y$_1$,Y$_2$,Y$_3$-alkyl)amino, (Y$_1$,Y$_2$,Y$_3$-aryl)amino, dihydroxyalkylamino, Y$_1$,Y$_2$,Y$_3$-alkoxy, (trihydroxyalkyl)alkoxy, (trihydroxyalkyl)alkylamino, (dicarboxyalkyl)amino, (Y$_1$,Y$_2$,Y$_3$-alkyl)thio, (X$_1$,X$_3$-aryl)thio, (Y$_1$,Y$_2$-alkyl)thio, (dihydroxyalkyl)thio, Y$_1$,Y$_2$-dioxoalkyl, or tri-(Y$_1$,Y$_2$,Y$_3$-methylaminocarboxyethyl)methylamino; and E$_3$ is ((glycosidyl)oxoheteroaryl)amino, ((glycosidyl)oxoaryl)amino, (X$_1$,X$_2$,X$_3$-heteroaryl)amino, (X$_1$-diarylketone)amino, (X,X$_1$-oxoaryl)amino, (X,X$_1$-dioxoaryl)amino, (Y$_1$-alkyl,Y$_2$-alkyldioxoheteroaryl) amino, (Y$_1$-alkyl,Y$_2$-alkyldioxoaryl)amino, (di(Y$_1$,Y$_2$-methyl)dioxoheteroaryl)amino, (di(Y$_1$,Y$_2$-methyl)dioxoaryl)amino, ((glycosidyl)heteroaryl)amino, ((glycosidyl)aryl)amino, ((carboxylacetylalkyl)oxoheteroaryl)amino, ((carboxylacetylalkyl)oxoaryl) amino, ((isopropylaminohydroxy-alkoxy)aryl)amino, (X$_1$,X$_2$,X$_3$-alkylaryl)amino, (X$_1$,X$_2$,X$_3$-heteroaryl)oxy, (isopropylaminohydroxyalkyl)aryloxy, (X$_1$,X$_2$,X$_3$-oxoheteroaryl)oxy, (X$_1$,X$_2$,X$_3$-oxoaryl)oxy, (X$_1$,Y$_1$-oxoheteroaryl)oxy, (X$_1$-diarylketone)oxy, (X,X$_1$-oxoaryl)oxy, (X$_1$,X$_2$-dioxoaryl)oxy, (Y$_1$,Y$_2$,di-aminodihydroxy)alkyl, (X$_1$,X$_2$-heteroaryl)thio, ((tricarboxylalkyl)ethylene-diamino)alkoxy, (X$_1$,X$_2$-oxoaryl)thio, (X$_1$,X$_2$-dioxoaryl)thio, (glycosidylheteroaryl)thio, (glycosidylaryl)thio, Y$_1$-alkyl(thiocarbonyl)thio, Y$_1$,Y$_2$-alkyl(thiocarbonyl)thio, Y$_1$,Y$_2$,Y$_3$-alkyl(thiocarbonyl)thio, (Y$_1$,Y$_2$-aminothiocarbonyl)thio, (pyranosyl)thio, cysteinyl, tyrosinyl, (phenylalainyl)amino, (dicarboxyalkyl)thio, (aminoaryl)$_{1-100}$amino, (pyranosyl)amino, (Y$_1$-aminoaryl)$_{1-100}$amino, (amino(sulfoaryl))$_{1-100}$amino, peptidyl, thymidinyl, uridinyl, guanosinyl, adenosinyl, cholesteryl, or biotinylalkoxy; wherein X is halide; each of X$_1$, X$_2$, and X$_3$, independently, is —Y$_1$, —O—Y$_1$, —S—Y$_1$, —NH—Y$_1$, —CO—O—Y$_1$, —O—CO—Y$_1$, —CO—NH—Y$_1$, —CO—NY$_1$Y$_2$, —NH—CO—Y$_1$, —SO$_2$—Y$_1$, —CHY$_1$Y$_2$, or —NY$_1$Y$_2$; and each of Y$_1$, Y$_2$, and Y$_3$, independently, is —Z or —B—Z;

each of x and y, independently, is 0 or 1; and s is 1–6;

provided that when x is 0, R$^1$ is =O; that when y is 0, R$^4$ is =O; that when x is 1, R$^1$ and R$^2$ join together to form C$_{6-40}$ aryl; and that when y is 1, R$^4$ and R$^5$ join together to form C$_{6-40}$ aryl; and or a salt thereof;

the method comprising:

reacting a compound of formula (II)

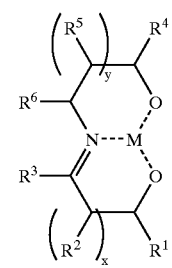

(II)

wherein M is a Cu, Mn, Fe, Co, Ni, Ru, Rh, Os, Zn, Cr, Ti, or Zr ion;

with a fullerene compound F$_f$ of the formula F(—K)$_m$(—Y—Z)$_q$ wherein the sum of q and m is 0 to form a compound of formula (III)

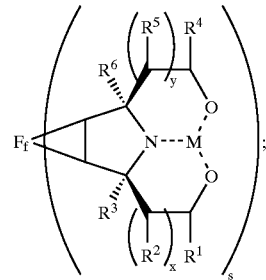

(III)

removing M from the compound of formula (III) to form a compound Of formula (I-A) wherein the sum of q and m is 0; and optionally treating the compound of formula (I-A) wherein the sum of q and m is 0 with a nitrating or sulfating agent to form a nitrofullerene or cyclosulfated fullerene, and contacting the nitrofullerene or cyclosulfated fullerene with a nucleophilic agent to form a compound of formula (I-A) wherein the sum of q and m is greater than 0.

25. The method of claim 24, wherein only one of x and y is 0.

26. The method of claim 25, wherein x is 1, y is 0, and R$^1$ and R$^2$ join together to form a benzene ring.

27. The method of claim 24, wherein both x and y are 0.

28. The method of claim 24, wherein M is a Cu ion.

29. The method of claim 24, wherein the compound of formula (II) is prepared by reacting a compound of formula (IV)

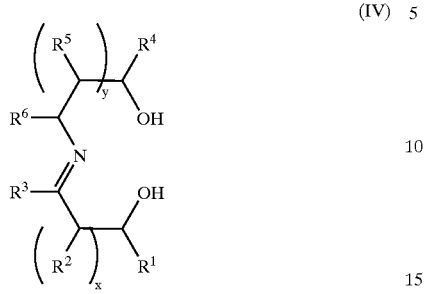

with a metal salt MX, wherein M has been defined above, and X is an anion.

30. The method of claim 29, wherein X is halide, sulfate, nitrate, or acetate.

31. The method of claim 29, wherein the compound of formula (IV) is prepared by reacting a compound of formula (V)

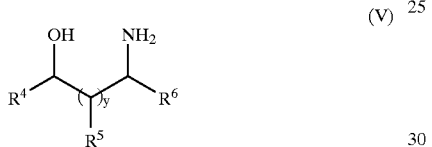

with a compound of formula (VI)

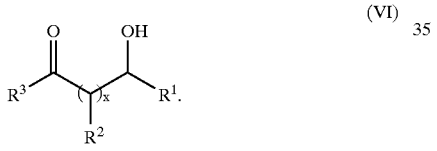

32. The method of claim 31, wherein each of $R^3$ and $R^6$, independently, is —H, —B—Z, —G—E, —G—CO—E, or a side chain of an amino acid, wherein B, E, G, and Z have been defined above.

33. A compound of formula (VII):

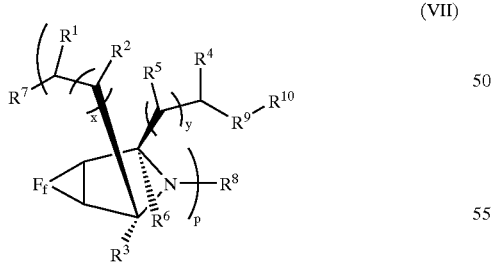

wherein $F_f$ is $F(—K)_m(—Y—Z)_q$ in which F is a fullerene core; each K, independently, is —OH, —SH, —NH$_2$, —NHOH, —SO$_3$H, —OSO$_3$H, —CO$_2$H, —CONH$_2$, —CONHNH$_2$, —P(OH)$_3$, —PO(OH)$_2$, —O—PO (OH)$_2$, —O—PO(OH)—O—PO(OH)$_2$, —O—PO (O$^-$)—O—CH$_2$CH$_2$—NH$_3^+$, —O—PO(O$^-$)—O—CH$_2$CH$_2$—N$^+$(CH$_3$)$_3$, -glycoside, —OCH$_3$, —OCH$_2$(CHOH)$_4$—CH$_2$OH, —OCH$_2$(CHOH)$_2$—CH$_2$OH, —NH—CH$_2$—CO$_2$H, —[CH(CO$_2$H)—CH$_2$]$_{1-100}$—OH, —[CH(CO$_2$R$^a$)—CH$_2$]$_{1-100}$—OH, —[C(CH$_3$)(CO$_2$H)—CH$_2$]$_{1-100}$—OH, —[C(CH$_3$)(CO$_2$ R$^a$)—CH$_2$]$_{1-100}$—OH, —N(OH)$_2$, —NH$_3^+$, —N$^+$H$_2$R$^a$, —N$^+$HR$^a$R$^b$, or —N$^+$R$^a$R$^b$R$^c$; each Y is —A—B—, in which A is —O—, —NH—, —S—, —CO—O—, —O—CO—, —O—CO—O—, —O—CO—NH—, —NH—CO—NH—, —CO—NH—, or —NH—CO—; and B is —R$^a$—[Si(CH$_3$)$_2$—O—]$_{1-100}$, C$_{1-2000}$ alkyl, C$_{6-40}$ aryl, C$_{7-2000}$ alkylaryl, C$_{7-2000}$ arylalkyl, (C$_{1-30}$ alkyl ether)$_{1-100}$, (C$_{6-40}$ aryl ether)$_{1-100}$, (C$_{7-2000}$ alkylaryl ether)$_{1-100}$, (C$_{7-2000}$ arylalkyl ether)$_{1-100}$, (C$_{1-30}$ alkyl thioether)$_{1-100}$, (C$_{6-40}$ aryl thioether)$_{1-100}$, (C$_{7-2000}$ alkylaryl thioether)$_{1-100}$, (C$_{7-2000}$ arylalkyl thioether)$_{1-100}$, (C$_{2-50}$ alkyl ester)$_{1-100}$, (C$_{7-2000}$ aryl ester)$_{1-100}$, (C$_{8-2000}$ alkylaryl ester)$_{1-100}$, (C$_{8-2000}$ arylalkyl ester)$_{1-100}$, —R$^a$—CO—O—(C$_{1-30}$ alkyl ether)$_{1-100}$, —R$^a$—CO—O—(C$_{6-40}$ aryl ether)$_{1-100}$, —R$^a$—CO—O—(C$_{7-2000}$ alkylaryl ether)$_{1-100}$, —R$^a$—CO—O—(C$_{7-2000}$ arylalkyl ether)$_{1-100}$, (C$_{4-50}$ alkyl urethane)$_{1-100}$, (C$_{14-60}$ aryl urethane)$_{1-100}$, (C$_{10-2000}$ alkylaryl urethane)$_{1-100}$, (C$_{10-2000}$ arylalkyl urethane)$_{1-100}$, (C$_{5-50}$ alkyl urea)$_{1-100}$, (C$_{14-60}$ aryl urea)$_{1-100}$, (C$_{10-2000}$ alkylaryl urea)$_{1-100}$, (C$_{10-2000}$ arylalkyl urea)$_{1-100}$, (C$_{2-50}$ alkyl amide)$_{1-100}$, (C$_{7-60}$ aryl amide)$_{1-100}$, (C$_{8-2000}$ alkylaryl amide)$_{1-100}$, (C$_{8-2000}$ arylalkyl amide)$_{1-100}$, (C$_{3-30}$ alkyl anhydride)$_{1-100}$, (C$_{8-50}$ aryl anhydride)$_{1-100}$, (C$_{9-2000}$ alkylaryl anhydride)$_{1-100}$, (C$_{9-2000}$ arylalkyl anhydride)$_{1-100}$, (C$_{2-30}$ alkyl carbonate)$_{1-100}$, (C$_{7-50}$ aryl carbonate)$_{1-100}$, (C$_{8-2000}$ alkylaryl carbonate)$_{1-100}$, (C$_{8-2000}$ arylalkyl carbonate)$_{1-100}$, —R$^a$—O—CO—NH—(R$^b$ or Ar—R$^b$—Ar)—NH—CO—O—(C$_{1-30}$ alkyl ether, C$_{6-40}$ aryl ether, C$_{7-2000}$ alkylaryl ether, or C$_{7-2000}$ arylalkyl ether)$_{1-100}$, —R$^a$—O—CO—NH—(R$^b$ or Ar—R$^b$—Ar)—NH—CO—O—(C$_{2-50}$ alkyl ester, C$_{7-60}$ aryl ester, C$_{8-2000}$ alkylaryl ester, or C$_{8-2000}$ arylalkyl ester)$_{1-100}$, —R$^a$—O—CO—NH—(R$^b$ or Ar—R$^b$—Ar)—NH—CO—O—(C$_{1-30}$ alkyl ether, C$_{6-40}$ aryl ether, C$_{7-2000}$ alkylaryl ether, or C$_{7-2000}$ arylalkyl ether)$_{1-100}$—CO—NH—(R$^b$ or Ar—R$^b$—Ar)—NH—CO—O—, —R$^a$—O—CO—NH—(R$^b$ or Ar—R$^b$—Ar)—NH—CO—O—(C$_{2-50}$ alkyl ester, C$_{7-60}$ aryl ester, C$_{8-2000}$ alkylaryl ester, or C$_{8-2000}$ arylalkyl ester)$_{1-100}$—R$^c$—O—CO—NH—(R$^b$ or Ar—R$^b$—Ar)—NH—CO—O—, —R$^a$—NH—CO—NH—(R$^b$ or Ar—R$^b$Ar)—NH—CO—O—(C$_{1-30}$ alkyl ether, C$_{6-40}$ aryl ether, C$_{7-2000}$ alkylaryl ether, or C$_{7-2000}$ arylalkyl ether)$_{1-100}$, —R$^a$—NH—CO—NH—(R$^b$ or Ar—R$^b$—Ar)—NH—CO—O—(C$_{2-50}$ alkyl ester, C$_{7-60}$ aryl ester, C$_{8-2000}$ alkylaryl ester, or C$_{8-2000}$ arylalkyl ester)$_{1-100}$, —R$^a$—NH—CO—NH—(R$^b$ or Ar—R$^b$—Ar)—NH—CO—O—(C$_{1-30}$ alkyl ether, C$_{6-40}$ aryl ether, C$_{7-2000}$ alkylaryl ether, or C$_{7-2000}$ arylalkyl ether)$_{1-100}$—CO—NH—(R$^b$ or Ar—R$^b$—Ar)—NH—CO—O—, —R$^a$—NH—CO—NH—(R$^b$ or Ar—R$^b$—Ar)—NH—CO—O—(C$_{2-50}$ alkyl ester, C$_{7-60}$ aryl ester, C$_{8-2000}$ alkylaryl ester, or C$_{8-2000}$ arylalkyl ester)$_{1-100}$—R$^c$—O—CO—NH—(R$^b$ or Ar—R$^b$—Ar)—NH—CO—O—, —R$^a$—O—CO—NH—(R$^b$ or Ar—R$^b$—Ar)—NH—CO—NH—(C$_{2-50}$ alkyl amide, C$_{7-60}$ aryl amide, C$_{8-2000}$ alkylaryl amide, or C$_{8-2000}$ arylalkyl amide)$_{1-100}$, —R$^a$—NH—CO—NH—(R$^b$ or Ar—R$^b$—Ar)—NH—CO—NH—(C$_{2-50}$ alkyl amide, C$_{7-60}$ aryl amide, C$_{8-2000}$ alkylaryl amide, or C$_{8-2000}$ arylalkyl amide)$_{1-100}$, or a bond; each Z, independently, is —G—D, wherein G is —R$^a$—, —R$^a$—Ar—, —Ar—R$^a$—, or —Ar—; and D is —H, —OH, —SH, —$NH_2$, —NHOH, —$SO_3H$, —$OSO_3H$, —$CO_2H$, —$CONH_2$, —$CONHNH_2$, —$CH(NH_2)$—$CO_2H$, —NH—$CH_2$—$CO_2H$, —$P(OH)_3$, —$PO(OH)_2$, —O—$PO(OH)_2$, —O—PO(OH)—O—$PO(OH)_2$, —O—PO(O$^-$)—O—$CH_2CH_2NH_3^+$, —O—PO(O$^-$)—O—$CH_2CH_2$—$N^+(CH_3)_3$, -glycoside, -oligosaccharide, —CO-glycoside, —CO-oligosaccharide, —$OCH_3$, —$OCH_2(CHOH)_4$—$CH_2OH$, —$OCH_2(CHOH)_2$—$CH_2OH$, —CO—$OCH_2(CHOH)_4$—$CH_2OH$, —$C_6H_3(OH)_2$, —$N(CH_2CO_2H)_2$, —CO—$N(CH_2CO_2H)_2$, —CO—NH—$C(CH_2CH_2CO_2H)_3$, —CO—NH—$C(CH_2CH_2OH)_3$, —$[CH_2$—$CH(CO_2R^a)]_{1-100}$—H, —$NH_3^+$, —$N^+H_2R^a$, —$N^+HR^aR^b$, or —$N^+R^aR^bR^c$, each of $R^a$, $R^b$, and $R^c$, independently, being $C_{1-20}$ alkyl and Ar being aryl; q is 0–30; and m is 0–30; provided that the sum of q and m is 0–30;

each of $R^1$ and $R^4$, independently, is =O or $C_{1-20}$ hydrocarbon; and each of $R^2$ and $R^5$, independently, is $C_{1-20}$ hydrocarbon; wherein $R^1$ and $R^2$, or $R^4$ and $R^5$ can join together to form $C_{6-40}$ aryl which is optionally substituted with halide, —OH, —$NHNH_2$, —$NH_2OH$, —NH—$CH_2$—$CO_2H$, —$CH_2$—$CH_2$—D, —$CH_2$—B—Z, —CO—$CH_2$—D, —CO—B—Z, —O—B—Z, or —NH—B—Z; each of B, D, and Z having been defined above;

each of $R^3$ and $R^6$, independently, is —H, —$CH_2$—D, —B—Z, —G—E, —G—CO—E or a side chain of an amino acid; each of B, D, and Z having been defined above, and E being $E_1$, $E_2$, or $E_3$, in which $E_1$ is $Y_1,Y_2$-amino, ($Y_1,Y_2$-alkyl)-amino, $Y_1,Y_2$-ethylenediamino, (dihydroxymethyl)alkylamino, ($X_1$, $X_3$-aryl)amino, or $X_1,X_3$-aryloxy; $E_2$ is $Y_1,Y_2$-alkoxy, ($Y_1,Y_2$-amino)alkoxy, ($Y_1,Y_2,Y_3$-aryl)oxy, (dihydroxyalkyl)-aryloxy, ($Y_1,Y_2,Y_3$-alkyl)amino, ($Y_1,Y_2,Y_3$-aryl)amino, dihydroxyalkylamino, $Y_1,Y_2,Y_3$-alkoxy, (trihydroxyalkyl)alkoxy, (trihydroxyalkyl)alkylamino, (dicarboxyalkyl)amino, ($Y_1,Y_2,Y_3$-alkyl)thio, ($X_1,X_3$-aryl)thio, ($Y_1,Y_2$-alkyl)thio, (dihydroxyalkyl)thio, $Y_1,Y_2$-dioxoalkyl, or tri-($Y_1,Y_2,Y_3$-methylaminocarboxyethyl)methylamino; and $E_3$ is ((glycosidyl)oxoheteroaryl)amino, ((glycosidyl)oxoaryl)amino, ($X_1,X_2,X_3$-heteroaryl)amino, ($X_1$-diarylketone)amino, ($X,X_1$-oxoaryl)amino, ($X,X_1$-dioxoaryl)amino, ($Y_1$-alkyl, $Y_2$-alkyldioxoheteroaryl) amino, ($Y_1$-alkyl, $Y_2$-alkyldioxoaryl)amino, (di($Y_1,Y_2$-methyl)dioxoheteroaryl)amino, (di($Y_1,Y_2$-methyl)dioxoaryl)amino, ((glycosidyl)heteroaryl)amino, ((glycosidyl)aryl)amino, ((carboxylacetylalkyl)oxoheteroaryl)amino, ((carboxylacetylalkyl)oxoaryl) amino, ((isopropylaminohydroxy-alkoxy)aryl)amino, ($X_1,X_2,X_3$-alkylaryl)amino, ($X_1,X_2,X_3$-heteroaryl)oxy, (isopropylaminohydroxyalkyl)aryloxy, ($X_1,X_2,X_3$-oxoheteroaryl)oxy, ($X_1,X_2,X_3$-oxoaryl)oxy, ($X_1,Y_1$-oxoheteroaryl)oxy, ($X_1$-diarylketone)oxy, ($X,X_1$-oxoaryl)oxy, ($X_1,X_2$-dioxoaryl)oxy, ($Y_1,Y_2$,di-aminodihydroxy)alkyl, ($X_1,X_2$-heteroaryl)thio, ((tricarboxylalkyl)ethylene-diamino)alkoxy, ($X_1,X_2$-oxoaryl)thio, ($X_1,X_2$-dioxoaryl)thio, (glycosidylheteroaryl)thio, (glycosidylaryl)thio, $Y_1$-alkyl(thiocarbonyl)thio, $Y_1,Y_2$-alkyl(thiocarbonyl)thio, $Y_1,Y_2,Y_3$-alkyl(thiocarbonyl)thio, ($Y_1,Y_2$-aminothiocarbonyl)thio, (pyranosyl)thio, cysteinyl, tyrosinyl, (phenylalainyl)amino, (dicarboxyalkyl)thio, (aminoaryl)$_{1-100}$amino, (pyranosyl)amino, ($Y_1$-aminoaryl)$_{1-100}$amino, (amino(sulfoaryl))$_{1-100}$amino, peptidyl, thymidinyl, uridinyl, guanosinyl, adenosinyl, cholesteryl, or biotinylalkoxy; wherein X is halide; each of $X_1$, $X_2$, and $X_3$, independently, is —$Y_1$, —O—$Y_1$, —S—$Y_1$, —NH—$Y_1$, —CO—O—$Y_1$, —O—CO—$Y_1$, —CO—NH—$Y_1$, —CO—$NY_1Y_2$, —NH—CO—$Y_1$, —$SO_2$—$Y_1$, —$CHY_1Y_2$, or —$NY_1Y_2$; and each of $Y_1$, $Y_2$, and $Y_3$, independently, is —Z or —B—Z; B and Z having been defined above;

$R^7$ is —$R^d$ or O—$R^e$; wherein $R^d$ is —OH, —OM, —$NHNH_2$, —NHOH, —NH—$CH_2$—$CO_2H$, —O—B—Z, —NH—B—Z, —E, —O—G—E, —NH—G—E, —O—G—CO—E, or —NH—G—CO—E; M being Cu, Mn, Fe, Co, Ni, Ru, Rh, Os, Zn, Cr, Ti, or Zr ion; and $R^e$ is —H, —$CH_2$—$CH_2$—D, —$CH_2$—B—Z, —$CH_2$—G—E, —$CH_2$—G—CO—E, —CO—$CH_2$—D, —CO—B—Z, —CO—G—E, or —CO—G—CO—E; each of B, D, E, G, and Z having been defined above;

$R^8$ is $R^e$;

$R^9$ is —O— or a bond;

$R^{10}$ is —$R^d$ or —$R^e$; each of which having been defined above;

each of x and y, independently, is 0 or 1; and p is 1–30;

provided that when x is 0, $R^1$ is =O, and $R^7$ is —$R^d$; that when y is 0, $R^4$ is =O, and $R^9$ is a bond, and $R^{10}$ is —$R^d$; that when x is 1, $R^1$ and $R^2$ join together to form $C_{6-40}$ aryl, and $R^7$ is —O—$R^e$; and that when y is 1, $R^4$ and $R^5$ join together to form $C_{6-40}$ aryl, $R^9$ is —O—, and $R^{10}$ is —$R^e$; and further provided that when p is greater than 1, x is 0; or a salt thereof.

34. The compound of claim 33, wherein F is $C_{60}$, $C_{61}$, $C_{62}$, $C_{63}$, $C_{64}$, $C_{65}$, $C_{70}$, $C_{76}$, $C_{78}$, $C_{82}$, $C_{84}$, or $C_{92}$, or La@$C_n$, Ho@$C_n$, Gd@$C_n$, or Er@$C_n$, in which n is 60, 74, or 82.

35. The compound of claim 33, wherein the sum of q and m is 0–20.

36. The compound of claim 33, wherein p is 2–10.

37. The compound of claim 33, wherein each of $R^3$ and $R^6$, independently, is —H. —B—Z, —G—E, —G—CO—E or a side chain of an amino acid.

38. The compound of claim 33, wherein $R^d$ is —OH, —$NHNH_2$, —E, —O—G—E, —NH—G—E, —O—G—CO—E, or —NH—G—CO—E.

39. The compound of claim 33, wherein $R^e$ is —H, —$CH_2$—G—E, —$CH_2$—G—CO—E, —CO—G—E, or —CO—G—CO—E.

40. The compound of claim 33, wherein both x and y are 0.

41. The compound of claim 40, wherein $R^d$ is —OH, —$NHNH_2$, —E, —O—G—E, —NH—G—E, —O—G—CO—E, or —NH—G—CO—E.

42. The compound of claim 41, wherein $R^e$ is —H, —$CH_2$—G—E, —$CH_2$—G—CO—E, —CO—G—E, or —CO—G—CO—E.

43. The compound of claim 42, wherein p is 2–10.

44. The compound of claim 43, said compound is oligo (1,3-dimethyl-fulleropyrrolidine-1,3-dicarboxylic N-amide).

45. A compound of formula (VIII):

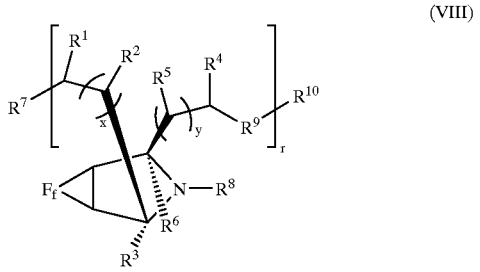

(VIII)

wherein $F_f$ is $F(-K)_m(-Y-Z)_q$ in which F is a fullerene core; each K, independently, is —OH, —SH, —NH$_2$, —NHOH, —SO$_3$H, —OSO$_3$H, —CO$_2$H, —CONH$_2$, —CONHNH$_2$, —P(OH)$_3$, —PO(OH)$_2$, —O—PO(OH)$_2$, —O—PO(OH)—O—PO(OH)$_2$, —O—PO(O$^-$)—O—CH$_2$CH$_2$—NH$_3^+$, —O—PO(O$^-$)—O—CH$_2$CH$_2$—N$^+$(CH$_3$)$_3$, -glycoside, —OCH$_3$, —OCH$_2$(CHOH)$_4$—CH$_2$OH, —OCH$_2$(CHOH)$_2$—CH$_2$OH, —NH—CH$_2$—CO$_2$H, —[CH(CO$_2$H)—CH$_2$]$_{1-100}$—OH, —[CH(CO$_2$R$^a$)—CH$_2$]$_{1-100}$—OH, —[C(CH$_3$)(CO$_2$H)—CH$_2$]$_{1-100}$—OH, —[C(CH$_3$)(CO$_2$R$^a$)—CH$_2$]$_{1-100}$—OH, —N(OH)$_2$, —NH$_3^+$, —N$^+$H$_2$R$^a$, —N$^+$HR$^a$R$^b$, or —N$^+$R$^a$R$^b$R$^c$; each Y is —A—B—, in which A is —O—, —NH—, —S—, —CO—O—, —O—CO—, —O—CO—O—, —O—CO—NH—, —NH—CO—NH—, —CO—NH—, or —NH—CO—; and B is —R$^a$—O—[Si(CH$_3$)$_2$—O—]$_{1-100}$, C$_{1-2000}$ alkyl, C$_{6-40}$ aryl, C$_{7-2000}$ alkylaryl, C$_{7-2000}$ arylalkyl, (C$_{1-30}$ alkyl ether)$_{1-100}$, (C$_{6-40}$ aryl ether)$_{1-100}$, (C$_{7-2000}$ alkylaryl ether)$_{1-100}$, (C$_{7-2000}$ arylalkyl ether)$_{1-100}$, (C$_{1-30}$ alkyl thioether)$_{1-100}$, (C$_{6-40}$ aryl thioether)$_{1-100}$, (C$_{7-2000}$ alkylaryl thioether)$_{1-100}$, (C$_{7-2000}$ arylalkyl thioether)$_{1-100}$, (C$_{2-50}$ alkyl ester)$_{1-100}$, (C$_{7-60}$ aryl ester)$_{1-100}$, (C$_{8-2000}$ alkylaryl ester)$_{1-100}$, (C$_{8-2000}$ arylalkyl ester)$_{1-100}$, —R$^a$—CO—O—(C$_{1-30}$ alkyl ether)$_{1-100}$, —R$^a$—CO—O—(C$_{6-40}$ aryl ether)$_{1-100}$, —R$^a$—CO—O—(C$_{7-2000}$ alkylaryl ether)$_{1-100}$, —R$^a$—CO—O—(C$_{7-2000}$ arylalkyl ether)$_{1-100}$, (C$_{4-50}$ alkyl urethane)$_{1-100}$, (C$_{14-60}$ aryl urethane)$_{1-100}$, (C$_{10-2000}$ alkylaryl urethane)$_{1-100}$, (C$_{10-2000}$ arylalkyl urethane)$_{1-100}$, (C$_{5-50}$ alkyl urea)$_{1-100}$, (C$_{14-60}$ aryl urea)$_{1-100}$, (C$_{10-2000}$ alkylaryl urea)$_{1-100}$, (C$_{10-2000}$ arylalkyl urea)$_{1-100}$, (C$_{2-50}$ alkyl amide)$_{1-100}$, (C$_{7-60}$ aryl amide)$_{1-100}$, (C$_{8-2000}$ alkylaryl amide)$_{1-100}$, (C$_{8-2000}$ arylalkyl amide)$_{1-100}$, (C$_{3-30}$ alkyl anhydride)$_{1-100}$, (C$_{8-50}$ aryl anhydride)$_{1-100}$, (C$_{9-2000}$ alkylaryl anhydride)$_{1-100}$, (C$_{9-2000}$ arylalkyl anhydride)$_{1-100}$, (C$_{2-30}$ alkyl carbonate)$_{1-100}$, (C$_{7-50}$ aryl carbonate)$_{1-100}$, (C$_{8-2000}$ alkylaryl carbonate)$_{1-100}$, (C$_{8-2000}$ arylalkyl carbonate)$_{1-100}$, —R$^a$—O—CO—NH—(R$^b$ or Ar—R$^b$—Ar)—NH—CO—O—(C$_{1-30}$ alkyl ether, C$_{6-40}$ aryl ether, C$_{7-2000}$ alkylaryl ether, or C$_{7-2000}$ arylalkyl ether)$_{1-100}$, —R$^a$—O—CO—NH—(R$^b$ or Ar—R$^b$—Ar)—NH—CO—O—(C$_{2-50}$ alkyl ester, C$_{7-60}$ aryl ester, C$_{8-2000}$ alkylaryl ester, or C$_{8-2000}$ arylalkyl ester)$_{1-100}$, —R$^a$—O—CO—NH—(R$^b$ or Ar—R$^b$—Ar)—NH—CO—O—(C$_{1-30}$ alkyl ether, C$_{6-40}$ aryl ether, C$_{7-2000}$ alkylaryl ether, or C$_{7-2000}$ arylalkyl ether)$_{1-100}$—CO—NH—(R$^b$ or Ar—R$^b$—Ar)—NH—CO—O—, —R$^a$—O—CO—NH—(R$^b$ or Ar—R$^b$—Ar)—NH—CO—O—(C$_{2-50}$ alkyl ester, C$_{7-60}$ aryl ester, C$_{8-2000}$ alkylaryl ester, or C$_{8-2000}$ arylalkyl ester)$_{1-100}$—R$^c$—O—CO—NH—(R$^b$ or Ar—R$^b$—Ar)—NH—CO—O—, —R$^a$—NH—CO—NH—(R$^b$ or Ar—R$^b$Ar)—NH—CO—O—(C$_{1-30}$ alkyl ether, C$_{6-40}$ aryl ether, C$_{7-2000}$ alkylaryl ether, or C$_{7-2000}$ arylalkyl ether)$_{1-100}$, —R$^a$—NH—CO—NH—(R$^b$ or Ar—R$^b$—Ar)—NH—CO—O—(C$_{2-50}$ alkyl ester, C$_{7-60}$ aryl ester, C$_{8-2000}$ alkylaryl ester, or C$_{8-2000}$ arylalkyl ester)$_{1-100}$, —R$^a$—NH—CO—NH—(R$^b$ or Ar—R$^b$—Ar)—NH—CO—O—(C$_{1-30}$ alkyl ether, C$_{6-40}$ aryl ether, C$_{7-2000}$ alkylaryl ether, or C$_{7-2000}$ arylalkyl ether)$_{1-100}$—CO—NH—(R$^b$ or Ar—R$^b$—Ar)—NH—CO—O—, —R$^a$—NH—CO—NH—(R$^b$ or Ar—R$^b$—Ar)—NH—CO—O—(C$_{2-50}$ alkyl ester, C$_{7-60}$ aryl ester, C$_{8-2000}$ alkylaryl ester, or C$_{8-2000}$ arylalkyl ester)$_{1-100}$—R$^c$—O—CO—NH—(R$^b$ or Ar—R$^b$—Ar)—NH—CO—O—, —R$^a$—O—CO—NH—(R$^b$ or Ar—R$^b$—Ar)—NH—CO—NH—(C$_{2-50}$ alkyl amide, C$_{7-60}$ aryl amide, C$_{8-2000}$ alkylaryl amide, or C$_{8-2000}$ arylalkyl amide)$_{1-100}$, —R$^a$—NH—CO—NH—(R$^b$ or Ar—R$^b$—Ar)—NH—CO—NH—(C$_{2-50}$ alkyl amide, C$_{7-60}$ aryl amide, C$_{8-2000}$ alkylaryl amide, or C$_{8-2000}$ arylalkyl amide)$_{1-100}$, or a bond; each Z, independently, is —G—D, wherein G is —R$^a$—, —R$^a$—Ar—, —Ar—R$^a$—, or —Ar—; and D is —H, —OH, —SH, —NH$_2$, —NHOH, —SO$_3$H, —OSO$_3$H, —CO$_2$H, —CONH$_2$, —CONHNH$_2$, —CH(NH$_2$)—CO$_2$H, —NH—CH$_2$—CO$_2$H, —P(OH)$_3$, —PO(OH)$_2$, —O—PO(OH)$_2$, —O—PO(OH)—O—PO(OH)$_2$, —O—PO(O$^-$)—O—CH$_2$CH$_2$NH$_3^+$, —O—PO(O$^-$)—O—CH$_2$CH$_2$—N$^+$(CH$_3$)$_3$, -glycoside, -oligosaccharide, —CO-glycoside, —CO-oligosaccharide, —OCH$_3$, —OCH$_2$(CHOH)$_4$—CH$_2$OH, —OCH$_2$(CHOH)$_2$—CH$_2$OH, —CO—OCH$_2$(CHOH)$_4$—CH$_2$OH, —C$_6$H$_3$(OH)$_2$, —N(CH$_2$CO$_2$H)$_2$, —CO—N(CH$_2$CO$_2$H)$_2$, —CO—NH—C(CH$_2$CH$_2$CO$_2$H)$_3$, —CO—NH—C(CH$_2$CH$_2$OH)$_3$, —[CH$_2$—CH(CO$_2$R$^a$)]$_{1-100}$—H, —NH$_3^+$, —N$^+$H$_2$R$^a$, —N$^+$HR$^a$R$^b$, or —N$^+$R$^a$R$^b$R$^c$, each of R$^a$, R$^b$, and R$^c$, independently, being C$_{1-20}$ alkyl and Ar being aryl; q is 0–30; and m is 0–30; provided that the sum of q and m is 0–30;

each of R$^1$ and R$^4$, independently, is =O or C$_{1-20}$ hydrocarbon; and each of R$^2$ and R$^5$, independently, is C$_{1-20}$ hydrocarbon; wherein R$^1$ and R$^2$, or R$^4$ and R$^5$ can join together to form C$_{6-40}$ aryl which is optionally substituted with halide, —OH, —NHNH$_2$, —NH$_2$OH, —NH—CH$_2$—CO$_2$H, —CH$_2$—CH$_2$—D, —CH$_2$—B—Z, —CO—CH$_2$—D, —CO—B—Z, —O—B—Z, or —NH—B—Z; each of B, D, and Z having been defined above;

each of R$^3$ and R$^6$, independently, is —H, —CH$_2$—D, —B—Z, —G—E, —G—CO—E or a side chain of an amino acid; each of B, D, and Z having been defined above, and E being E$_1$, E$_2$, or E$_3$, in which E$_1$ is Y$_1$,Y$_2$-amino, (Y$_1$,Y$_2$-alkyl)-amino, Y$_1$,Y$_2$-ethylenediamino, (dihydroxymethyl)alkylamino, (X$_1$, X$_3$-aryl)amino, or X$_1$,X$_3$-aryloxy; E$_2$ is Y$_1$,Y$_2$-alkoxy, (Y$_1$,Y$_2$-amino)alkoxy, (Y$_1$,Y$_2$,Y$_3$-aryl)oxy, (dihydroxyalkyl)-aryloxy, (Y$_1$,Y$_2$,Y$_3$-alkyl)amino, (Y$_1$,Y$_2$,Y$_3$-aryl)amino, dihydroxyalkylamino, Y$_1$,Y$_2$, Y$_3$-alkoxy, (trihydroxyalkyl)alkoxy, (trihydroxyalkyl)alkylamino, (dicarboxyalkyl)amino, (Y$_1$,Y$_2$,Y$_3$-alkyl)thio, (X$_1$,X$_3$-aryl)thio, (Y$_1$,Y$_2$-alkyl)thio, (dihydroxyalkyl)thio, Y$_1$,Y$_2$-dioxoalkyl, or tri-(Y$_1$,Y$_2$, Y$_3$-methylaminocarboxyethyl)methylamino; and E$_3$ is ((glycosidyl)oxoheteroaryl)amino, ((glycosidyl)oxoaryl)amino, (X$_1$,X$_2$,X$_3$-heteroaryl)amino, (X$_1$-diarylketone)amino, (X,X$_1$-oxoaryl)amino, (X,X$_1$-dioxoaryl)amino, (Y$_1$-alkyl, Y$_2$-alkyldioxoheteroaryl)

amino, ($Y_1$-alkyl, $Y_2$-alkyldioxoaryl)amino, (di($Y_1,Y_2$-methyl)dioxoheteroaryl)amino, (di($Y_1,Y_2$-methyl)dioxoaryl)amino, ((glycosidyl)heteroaryl)amino, ((glycosidyl)aryl)amino, ((carboxylacetylalkyl)oxoheteroaryl)amino, ((carboxylacetylalkyl)oxoaryl)amino, ((isopropylaminohydroxy-alkoxy)aryl)amino, ($X_1,X_2,X_3$-alkylaryl)amino, ($X_1,X_2,X_3$-heteroaryl)oxy, (isopropylaminohydroxyalkyl)aryloxy, ($X_1,X_2,X_3$-oxoheteroaryl)oxy, $X_1,X_2,X_3$-oxoaryl)oxy, ($X_1,Y_1$-oxoheteroaryl)oxy, ($X_1$-diarylketone)oxy, ($X,X_1$-oxoaryl)oxy, ($X_1,X_2$-dioxoaryl)oxy, ($Y_1,Y_2$,diaminodihydroxy)alkyl, ($X_1,X_2$-heteroaryl)thio, ((tricarboxylalkyl)ethylene-diamino)alkoxy, ($X_1,X_2$-oxoaryl)thio, ($X_1,X_2$-dioxoaryl)thio, (glycosidylheteroaryl)thio, (glycosidylaryl)thio, $Y_1$alkyl(thiocarbonyl)thio, $Y_1,Y_2$-alkyl(thiocarbonyl)thio, $Y_1,Y_2,Y_3$-alkyl(thiocarbonyl)thio, ($Y_1,Y_2$-aminothiocarbonyl)thio, (pyranosyl)thio, cysteinyl, tyrosinyl, (phenylalainyl)amino, (dicarboxyalkyl)thio, (aminoaryl)$_{1-100}$amino, (pyranosyl)amino, ($Y_1$-aminoaryl)$_{1-100}$amino, (amino(sulfoaryl))$_{1-100}$amino, peptidyl, thymidinyl, uridinyl, guanosinyl, adenosinyl, cholesteryl, or biotinylalkoxy; wherein X is halide; each of $X_1$, $X_2$, and $X_3$, independently, is —$Y_1$, —O—$Y_1$, —S—$Y_1$, —NH—$Y_1$, —CO—O—$Y_1$, —O—CO—$Y_1$, —CO—NH—$Y_1$, —CO—N$Y_1Y_2$, —NH—CO—$Y_1$, —SO$_2$—$Y_1$, —CH$Y_1Y_2$, or —N$Y_1Y_2$; and each of $Y_1$, $Y_2$, and $Y_3$, independently, is —Z or —B—Z; B and Z having been defined above;

$R^7$ is —$R^d$ or —O—$R^e$; wherein $R^d$ is —OH, —OM, —NHNH$_2$, —NHOH, —NH—CH$_2$—CO$_2$H, —O—B—Z, —NH—B—Z, —E, —O—G—E, —NH—G—E, —O—G—CO—E, or —NH—G—CO—E; M being Cu, Mn, Fe, Co, Ni, Ru, Rh, Os, Zn, Cr, Ti, or Zr ion; and $R^e$ is —H, —CH$_2$—CH$_2$—D, —CH$_2$—B—Z, —CH$_2$—G—E, —CH$_2$—G—CO—E, —CO—CH$_2$—D, —CO—B—Z, —CO—G—E, or —CO—G—CO—E; each of B, D, E, G, and Z having been defined above;

$R^8$ is $R^e$, which has the same meaning as set forth above;

$R^9$ is —O—$R^f$— or —$R^g$—; wherein $R^f$ is —CO—B—G—O—, —CO—B—G—NH—, —CO—B—G—CO—O—, or —CO—B—G—CO—NH—; and $R^g$ is —NH—, —O—, —O—B—G—O—, —NH—B—G—O—, —NH—B—G—NH—, —O—CO—B—G—CO—O—, or —NH—CO—B—G—CO—NH—; B and G having been defined above;

$R^{10}$ is —H;

each of x and y, independently, is 0 or 1; and r is 1–100;

provided that when x is 0, $R^1$ is =O, and $R^7$ is —$R^d$; that when y is 0, $R^4$ is =O, and $R^9$ is —$R^g$, and $R^{10}$ is —H; that when x is 1, $R^1$ and $R^2$ join together to form $C_{6-40}$ aryl, and $R^7$ is —O—$R^e$; and that when y is 1, $R^4$ and $R^5$ join together to form $C_{6-40}$ aryl, $R^9$ is —O—$R^f$, and $R^{10}$ is —H; and further provided that when r is greater than 1, x is 0;

or a salt thereof.

46. The compound of claim 45, wherein F is $C_{60}$, $C_{61}$, $C_{62}$, $C_{63}$, $C_{64}$, $C_{65}$, $C_{70}$, $C_{76}$, $C_{78}$, $C_{82}$, $C_{84}$, or $C_{92}$, or La@$C_n$, Ho@$C_n$, Gd@$C_n$, or Er@$C_n$, in which n is 60, 74, or 82.

47. The compound of claim 45, wherein the sum of q and m is 0–20.

48. The compound of claim 45, wherein r is 2–30.

49. The compound of claim 45, wherein each of $R^3$ and $R^6$, independently, is —H, —B—Z, —G—E, —G—CO—E, or a side chain of an amino acid.

50. The compound of claim 45, wherein $R^d$ is —OH, —NHNH$_2$, —E, —O—G—E, —NH—G—E, —O—G—CO—E, or —NH—G—CO—E.

51. The compound of claim 45, wherein $R^e$ is —H, —CH$_2$—G—E, —CH$_2$—G—CO—E, —CO—G—E, or —CO—G—CO—E.

52. The compound of claim 45, wherein $R^f$ is —CO—B—G—NH— or —CO—B—G—CO—NH—.

53. The compound of claim 45, wherein $R^g$ is —O—B—G—O—, —NH—B—G—O—, —NH—B—G—NH—, —O—CO—B—G—CO—O—, or —NH—CO—B—G—CO—NH—.

54. The compound of claim 45, wherein both x and y are 0.

55. The compound of claim 54, wherein each of $R^3$ and $R^6$; independently, is —H, —B—Z, —G—E, —G—CO—E, or a side chain of an amino acid.

56. The compound of claim 55, wherein $R^d$ is —OH, —NHNH$^2$, —E, —O—G—E, —NH—G—E, —O—G—CO—E, or —NH—G—CO—E.

57. The compound of claim 56, wherein $R^e$ is —H, —CH$_2$—G—E, —CH$_2$—G—CO—E, —CO—G—E, or —CO—G—CO—E.

58. The compound of claim 57, wherein $R^f$ is —CO—B—G—NH— or —CO—B—G—CO—NH—.

59. The compound of claim 58, wherein $R^g$ is —O—B—G—O—, —NH—B—G—O—, —NH—B—G—NH—, —O—CO—B—G—CO—O—, or —NH—CO—B—G—CO—NH—.

60. The compound of claim 59, wherein r is 2–30.

* * * * *